United States Patent
Douglas et al.

(10) Patent No.: US 11,328,215 B2
(45) Date of Patent: *May 10, 2022

(54) COMPUTER IMPLEMENTED DETERMINATION METHOD AND SYSTEM

(71) Applicant: BABYLON PARTNERS LIMITED, London (GB)

(72) Inventors: Laura Helen Douglas, London (GB); Pavel Myshkov, London (GB); Robert Walecki, London (GB); Iliyan Radev Zarov, London (GB); Konstantinos Gourgoulias, London (GB); Christopher Lucas, London (GB); Christopher Robert Hart, London (GB); Adam Philip Baker, London (GB); Maneesh Sahani, London (GB); Iurii Perov, London (GB); Saurabh Johri, London (GB)

(73) Assignee: Babylon Partners Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/277,975

(22) Filed: Feb. 15, 2019

(65) Prior Publication Data
US 2019/0180841 A1 Jun. 13, 2019

Related U.S. Application Data

(63) Continuation of application No. 16/325,681, filed as application No. PCT/GB2018/053154 on Oct. 31, 2018.

(30) Foreign Application Priority Data

Oct. 31, 2017 (GB) .................................. 1718003
Sep. 27, 2018 (GB) .................................. 1815800

(51) Int. Cl.
*G06N 7/00* (2006.01)
*G16H 50/20* (2018.01)
(Continued)

(52) U.S. Cl.
CPC ............. *G06N 7/005* (2013.01); *G06F 17/16* (2013.01); *G06N 3/0454* (2013.01); *G06N 3/08* (2013.01);
(Continued)

(58) Field of Classification Search
CPC .......... G06N 7/005; G06N 5/04; G06N 3/082; G06N 3/08; G06N 3/0454; G06N 20/20;
(Continued)

(56) References Cited

U.S. PATENT DOCUMENTS 5,463,548 A 10/1995 Asada et al.
8,068,993 B2 * 11/2011 Karlov .................. G16H 50/30
702/19
(Continued)

OTHER PUBLICATIONS

Lisboa and Taktak, The use of artificial neural networks in decision support in cancer: A systematic review, 19(4) Neural Networks 408-415 (May 2006) (Year: 2006).*

(Continued)

*Primary Examiner* — Evangeline Barr
*Assistant Examiner* — Jordan L Jackson
(74) *Attorney, Agent, or Firm* — McDermott Will & Emery LLP

(57) ABSTRACT

Methods for providing a computer implemented medical diagnosis are provided. In one aspect, a method includes receiving an input from a user comprising at least one symptom of the user, and providing the at least one symptom as an input to a medical model. The method also includes deriving estimates of the probability of the user having a disease from the discriminative model, inputting the esti- (Continued)

mates to the inference engine, performing approximate inference on the probabilistic graphical model to obtain a prediction of the probability that the user has that disease, and outputting the probability of the user having the disease for display by a display device.

17 Claims, 11 Drawing Sheets

(51) Int. Cl.
    *G16H 50/70*     (2018.01)
    *G06N 3/04*     (2006.01)
    *G16H 50/30*     (2018.01)
    *G06N 20/20*     (2019.01)
    *G06F 17/16*     (2006.01)
    *G06N 3/08*     (2006.01)
    *G06N 5/04*     (2006.01)
    *G16B 45/00*     (2019.01)
    *G16B 5/20*     (2019.01)
    *G16H 50/50*     (2018.01)

(52) U.S. Cl.
    CPC .............. *G06N 5/04* (2013.01); *G06N 20/20* (2019.01); *G16B 5/20* (2019.02); *G16B 45/00* (2019.02); *G16H 50/20* (2018.01); *G16H 50/30* (2018.01); *G16H 50/70* (2018.01); *G06N 3/082* (2013.01); *G16H 50/50* (2018.01)

(58) Field of Classification Search
    CPC ........ G16H 50/70; G16H 50/30; G16H 50/20; G06F 17/16
    See application file for complete search history.

(56) References Cited

U.S. PATENT DOCUMENTS

| | | | | |
|---|---|---|---|---|
| 10,026,508 B2* | 7/2018 | Silva | ................... | G06Q 10/101 |
| 2004/0193036 A1 | 9/2004 | Zhou et al. | | |
| 2006/0155660 A1* | 7/2006 | Koshizen | ............. | G05B 13/027 |
| | | | | 706/18 |
| 2009/0024332 A1 | 1/2009 | Karlov et al. | | |
| 2010/0145897 A1 | 6/2010 | Semizarov et al. | | |
| 2011/0098187 A1 | 4/2011 | Urdea et al. | | |
| 2013/0171649 A1 | 7/2013 | Mayr | | |
| 2014/0035937 A1* | 2/2014 | Stefansson | ............ | G06F 9/5072 |
| | | | | 345/505 |
| 2015/0347676 A1 | 12/2015 | Zhao et al. | | |
| 2016/0135706 A1 | 5/2016 | Sullivan et al. | | |
| 2017/0061324 A1 | 3/2017 | Glass et al. | | |
| 2017/0261520 A1 | 9/2017 | Urdea et al. | | |
| 2017/0323075 A1 | 11/2017 | Krause et al. | | |
| 2017/0342477 A1 | 11/2017 | Jensen et al. | | |
| 2018/0233233 A1 | 8/2018 | Sharma et al. | | |
| 2019/0271709 A1 | 9/2019 | Eden et al. | | |
| 2019/0380592 A1 | 12/2019 | Priyankara et al. | | |
| 2020/0143922 A1 | 5/2020 | Chekroud et al. | | |
| 2021/0212629 A1 | 7/2021 | Li et al. | | |

OTHER PUBLICATIONS

Halpern and Sontag, Unsupervised Learning of Noisy-OR Bayesian Networks, Proceedings of the Twenty-Ninth Conference on Uncertainty in Artificial Intelligence (Sep. 26, 2013) (Year: 2013).*
Wang et al., Computer-assisted diagnosis of breast cancer using a data-driven Bayesian belief network, 54 Int J of Med Informatics 115-126 (Year: 1998).*
Howes and Thomas, Chapter 37. Efficient Random Number Generation and Application Using CUDA, GPU Gems 3 (Aug. 12, 2007) (Year: 2007).*
Jenkins and Peterson, GPU Accelerated Stochastic Simulation, Conference: Symposium on Application Accelerators in High Performance Computing (SAAHPC)(Jul. 2010) (Year: 2010).*
Park, An Analysis of GPU Parallel Computing, 2009 DOD High Performance Computing Modernization Program Users Group Conference 366 § Compute Unified Device Architecture (CUDA) Programming (Mar. 2, 2010) (Year: 2010).*
Linderman et al., High-throughput Bayesian Network Learning using Heterogeneous Multicore Computers, ICS Author manuscript (Jun. 2010) (Year: 2010).*
Hong et al., Accelerating CUDA Graph Algorithms at Maximum Warp, Proceedings of the 16th ACM symposium on Principles and practice of parallel programming (Year: 2011).*
International Preliminary Report on Patentability and Written Opinion issued in corresponding International Application No. PCT/GB2018/053154, dated May 5, 2020.
Quad Morris, "Recognition Networks for Approximate Inference in BN20 Networks", Proceedings of the Seventeenth Conference on Uncertainty in Artificial Intelligence, Aug. 2, 2011, pp. 370-377.
Pascal Vincent et al., "Stacked Denoising Autoencoders: Learning Useful Representations in a Deep Network with a Local Denoising Criterion", Journal of Machine Learning Research, vol. 11, Dec. 1, 2010, pp. 3371-3408.
BaiFang Zhang et al., "Protein secondary structure prediction using machine learning", The 2013 International Joint Conference on Neural Networks (IJCNN), vol. 1, Jan. 1, 2005, pp. 532-537.
Dacheng Tao et al., "Bayesian tensor analysis", The 2013 International Joint Conference on Neural Networks (IJCNN), Jun. 1, 2008, pp. 1402-1409.
Lennart F. Hoogerheide et al., "On the shape of posterior densities and credible sets in instrumental variable regression models with reduced rank: An application of flexible sampling methods using neural networks", Journal of Econometrics, Elsevier Science, vol. 139, No. 1, May 16, 2007, pp. 154-180.
Malcolm Pradhan et al., "Knowledge Engineering for Large Belief Networks", Uncertainty Proceedings 1994, Jan. 1, 1994, pp. 484-490.
Quaid Morris: "Recognition networks for approximate inference in BN20 Networks", proceedings of the Seventeenth conference on Uncertainty in artificial intelligence, Aug. 2, 2011, pp. 370-377, XP055547941, San Francisco, CA, USA.
Pascal Vincent et al: "stacked denoising autoencoders: Learning useful representation in a deep network with a local denoising criterion", journal of machine learning research, MIT press, Cambridge, MA, US vol. 11, Dec. 1, 2010, pp. 3371-3408, XP058336476.
Baifang Zhang et al: "Protein secondary structure prediction using machine learning", the 2013 International joint conference on neural networks (IJCNN), vol. 1, Jan. 1, 2005, p. 632, XP055549370.
Dacheng Tao et al: "Protein secondary structure prediction using machine learning", the international joint conference on neural networks (IJCNN), Jun. 1, 2008, pp. 1402-1409, XP055549421.
Hoogerheide et al: "on the shape of posterior densities and credible sets in instrumental variable regression models with reduced rank: an application of flexible sampling methods using neural networks", Journal of econometrics, Elsevier science, Amsterdam, NL, vol. 139, No. 1, May 16, 2007, pp. 154-180, XP022081163.
Malcolm Pradhan et al: "Knowledge engineering for large belief networks", in: "Uncertainty proceedings 1994", Jan. 1, 1994, Elsevier, XP055548802.
Kurt Hornik, et al,, Multilayer feedforward networks are universal approximators. Neural networks, 2(5):359-366, 1989.
Daphne Koller, et al., Probabilistic graphical models: principles and techniques. MIT press, 2009. (6 parts).
Radford M Neal. Annealed importance sampling. Statistics and computing, 11(2):125-139, 2001.
Brooks Paige, et al., Inference networks for sequential monte carlo in graphical models. In International Conference on Machine Learning, pp. 3040-3049, 2016.
Marco Saerens, et al., Any reasonable cost function can be used for a posteriori probability approximation. IEEE transactions on neural networks, 13(5): 1204-1210, 2002.
Naftali Tishby, et al., The information bottleneck method. arXiv preprint physics/0004057, 2000.

(56) References Cited

OTHER PUBLICATIONS

Martin J Wainwright, et al., Graphical models, exponential families, and variational inference. Foundations and Trends in Machine Learning, 1(1-2):1-305, 2008.
Mathieu Germain, et al., "MADE: masked autoencoder for distribution estimation", arXiv, Jun. 2015.
George Papamakarios, et al., "Fast free Inference of Simulation Models with Bayesian Conditional Density Estimation", arXiv, Apr. 2, 2018.
Tuan Anh Le, et al., "Using Synthetic Data to Train Neural Networks is Model-Based Reasoning" arXiv, Mar. 2, 2017.
Jian Cheng, et al., Ais-bn: An adaptive importance sampling algorithm for evidential reasoning in large bayesian networks. Journal of Artificial Intelligence Research, 2000.
Samuel Gershman, et al., Amortized inference in probabilistic reasoning. In Proceedings of the Cognitive Science Society, vol. 36, 2014.
Shixiang Gu, et al., Neural adaptive sequential monte carlo. In Advances in Neural Information Processing Systems, pp. 2629-2637, 2015.
Changhe Yuan, et al., Importance sampling algorithms for bayesian networks: Principles and performance. Mathematical and Computer Modelling, 43(9):1189-1207, 2006.
Written Opinion of PCT/GB2018/053154, dated May 9, 2019, 17 pages.
International Search Report for PCT/GB2018/053154, dated May 9, 2019, 4 pages.
Notice of Allowance issued in related U.S. Appl. No. 16/277,970, dated Oct. 18, 2021.
Non-Final Rejection issued in related U.S. Appl. No. 16/277,956, dated Feb. 11, 2022.

* cited by examiner (a) Directed Graphical Model (b) UM architecture

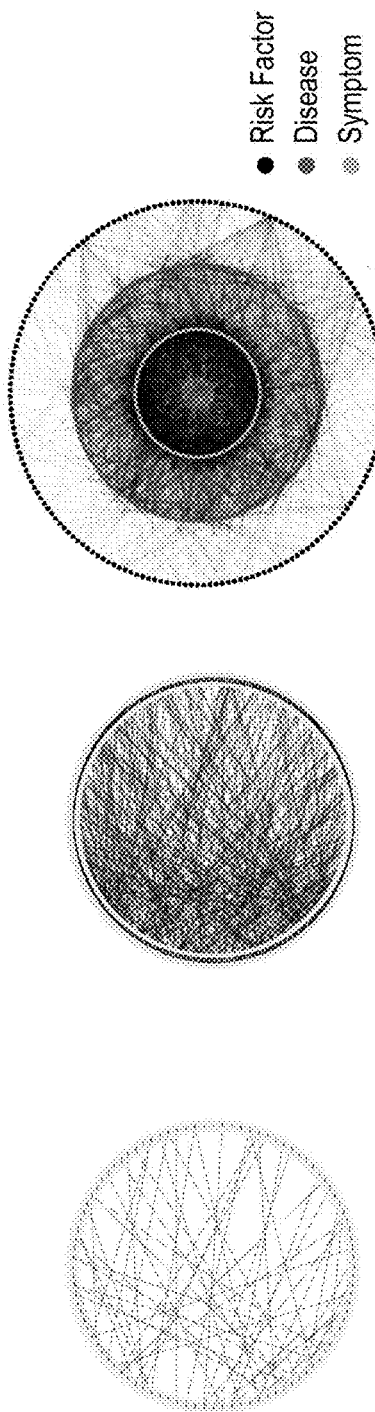
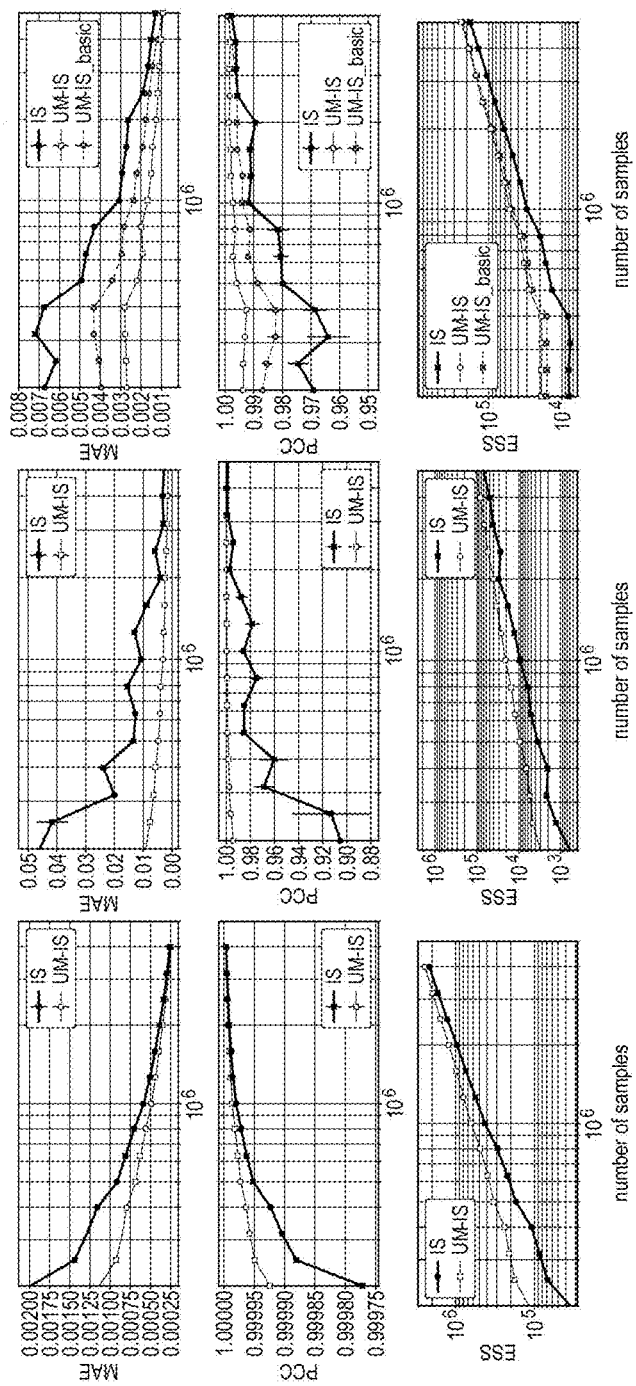
Fig. 10(a) Synthetic graph, 96 nodes. (b) Synthetic graph, 768 nodes. (c) Medical PGM, (~1200 nodes.)

(a) Diabetes embeddings.

(b) Smoke, Obesity embeddings.

COMPUTER IMPLEMENTED DETERMINATION METHOD AND SYSTEM

CROSS-REFERENCE TO RELATED APPLICATIONS

This application claims the benefit of priority under 35 U.S.C. § 120 to and is a continuation of U.S. patent application Ser. No. 16/325,681, filed on Feb. 14, 2019, which application is the U.S. national stage under 35 U.S.C. § 371 of International Application Number PCT/GB2018/053154, having an international filing date of Oct. 31, 2018, which claims benefit of priority to Great Britain Patent Application Number 1718003.5, filed Oct. 31, 2017, and to Great Britain Patent Application Number 1815800.6, filed Sep. 27, 2018, all of which applications are incorporated herein by reference. This application is also related to U.S. patent application Ser. No. 16/277,970, filed concurrently on Feb. 15, 2019; and is also related to U.S. patent application Ser. No. 16/277,956, filed concurrently on Feb. 15, 2019.

FIELD

Embodiments of the present invention relate to the field of computer implemented determination methods and systems.

BACKGROUND

Graphical models provide a natural framework for expressing the probabilistic relationships between random variables in numerous fields across the natural sciences. Bayesian networks, a directed form of graphical model, have been used extensively in medicine, to capture causal relationships between entities such as risk-factors, diseases and symptoms, and to facilitate medical decision-making tasks such as disease diagnosis. Key to decision-making is the process of performing probabilistic inference to update one's prior beliefs about the likelihood of a set of diseases, based on the observation of new evidence.

BRIEF DESCRIPTION OF FIGURES

FIG. 10 shows the performance of the above system on three different graphical models. FIG. 10($a$) shows results from a synthetic graph with 96 nodes, FIG. 10($b$) shows results from a synthetic graph with 768 nodes and FIG. 10($c$) shows results from a medical probabilistic graphical model (PGM). Inference was applied through importance sampling with and without the support of a trained UM and it was evaluated in terms of Pearson Correlation Coefficient (PCC), Mean Absolute Error (MAE) and Effective Sampling Size (ESS); FIG. 11($a$) shows results for Diabetes embeddings and FIG. 11($b$) shows results for smoke and obesity embeddings. The display embedding vectors correspond to the first two components. It can be seen that they separate quite well unrelated medical concepts and show an overlap for concepts which are closely related.

DETAILED DESCRIPTION

Figure 1:
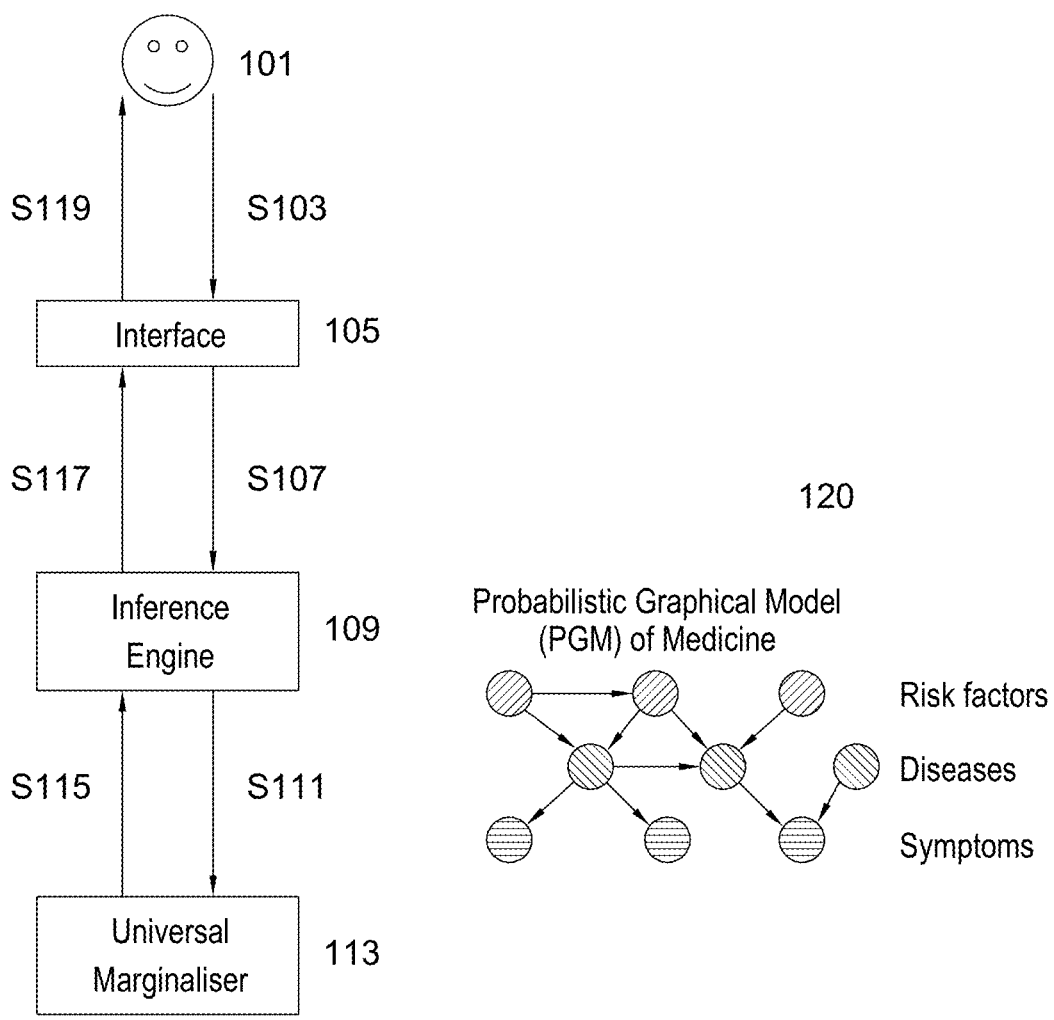
FIG. 1 is an overview of a system in accordance with an embodiment.

In an embodiment, a method for providing a computer implemented medical diagnosis is provided, the method comprising: receiving an input from a user comprising at least one symptom; providing at least one symptom as an input to a medical model; using the medical model to determine the probability of the user having a disease stored in the medical model from the provided input; and outputting the probability of the user having one or more diseases, wherein said medical model comprises a probabilistic graphical model containing the probability distributions and the relationships between symptoms and diseases, an inference engine configured to perform Bayesian inference on said probabilistic graphical model using a discriminative model, wherein the discriminative model has been pre-trained to approximate the probabilistic graphical model, the discriminative model being trained using samples generated from said probabilistic graphical model, wherein some of the data of the samples has been masked to allow the discriminative model to produce data which is robust to the user providing incomplete information about their symptoms, and wherein determining the probability that the user has a disease comprises deriving estimates of the probabilities that the user has that disease from the discriminative model, inputting these estimates to the inference engine and performing approximate inference on the probabilistic graphical model to obtain a prediction of the probability that the user has that disease.

Medical diagnosis systems require significant computing resources such as processor capacity. The disclosed systems and methods solve this technical problem with a technical solution, namely by conducting approximate statistical inference on a PGM with help of a discriminative model (e.g. a neural net) to provide an estimate of the posterior probabilities. The discriminative model is trained such that it is robust to the user providing incomplete information about their symptoms. The above therefore allows the system to produce answers using such new approximate inference with the accuracy comparable to using exact or already existing approximate inference techniques, but in a fraction of the time and with a reduction in the processing required.

The inference engine may be configured to perform importance sampling over conditional marginal. However, other methods may be used such as Variational Inference, other Monte Carlo methods, etc.

The discriminative model can be a neural network. In some embodiments, the neural network is a single neural network in other embodiments the neural network is as described in Further Embodiment A. The neural net can approximate the outputs of the probabilistic graphical model and hence later in this document, it is termed a Universal Marginaliser (UM). In an embodiment, the probabilistic graphical model is a noisy-OR model.

As, performing probabilistic inference is computationally expensive, and in a medicine where large-scale Bayesian networks are required to make clinically robust diagnoses, it is not feasible to apply exact inference techniques. Instead, approximate, sampling-based algorithms are used which provide theoretical guarantees (under the central limit theorem) regarding convergence to the true posterior. In the context of medical diagnosis, this amounts to arriving at the true disease differential, based on the evidence and the underlying the model.

As the true 'target' (posterior) distribution is unknown ahead of time, the task of inference is to sample from an independent 'proposal' distribution, which, ideally is as close as possible to the target. The standard approach when applying Bayesian networks for medical decision-making, is to use the model prior as the proposal distribution. However, this is often not ideal, particularly in cases where an unusual combination of symptoms is generated by a rare disease. In these and similar cases, a large number of samples is often required to reduce the variance in the estimate of the true posterior; this poses a significant practical constraint to the use sampling algorithms for inference.

As a consequence, in all but the simplest of symptom presentations, it is often difficult to match the diagnostic speed of human doctors. This is because, for cognitive tasks, humans operate in the setting of amortized inference i.e. 'they have to solve many similar inference problems, and can thus offload part of the computational work to shared pre-computation and adaptation over time'. As discussed above, where the proposal is close to posterior, fewer samples need to be drawn, and therefore inference will be more rapid.

FIG. 1 is a schematic of a method in accordance with an embodiment. A patient 101 inputs their symptoms in step S103 via interface 105. The patient may also input their risk factors, for example, whether they are a smoker, their weight, etc. The interface may be adapted to ask the patient 101 specific questions. Alternately, the patient may just simply enter free text. The patient's risk factors may be derived from the patient's records held in a database (not shown). Therefore, once the patient identified themselves, data about the patient could be accessed via the system.

In further embodiments, follow-up questions may be asked by the interface 105. How this is achieved will be explained later. First, it will be assumed that the patient provide all possible information (evidence) to the system at the start of the process. This will be used to explain the basic procedure. However, a variation on the procedure will then be explained with patient only gives partial information with the system, once completing the first analysis, requests further information.

The evidence will be taken to be the presence or absence of all known symptoms and risk factors. For symptoms and risk factors where the patient has been unable to provide a response, these will assume to be unknown.

Next, this evidence is passed in step S107 to the inference engine 109. Inference engine 109 performs Bayesian inference on PGM 120. PGM 120 will be described in more detail with reference to FIG. 2 after the discussion of FIG. 1.

Due to the size of the PGM 120, it is not possible to perform exact inference using inference engine 109 in a realistic timescale. Therefore, the inference engine 109 performs approximate inference. In an embodiment, the inference engine 109 is configured to perform Importance Sampling. Importance sampling is described with reference to equation 3 below.

When performing approximate inference, the inference engine 109 requires an approximation of the probability distributions within the PGM to act as proposals for the sampling. In step S111, the evidence is passed to what would be termed a universal marginaliser (UM) 113. The UM will be described in more detail with reference to both FIGS. 3 and 4. In summary, the UM is a neural network that has been trained to approximate the outputs of the PGM 120.

Figure 3:
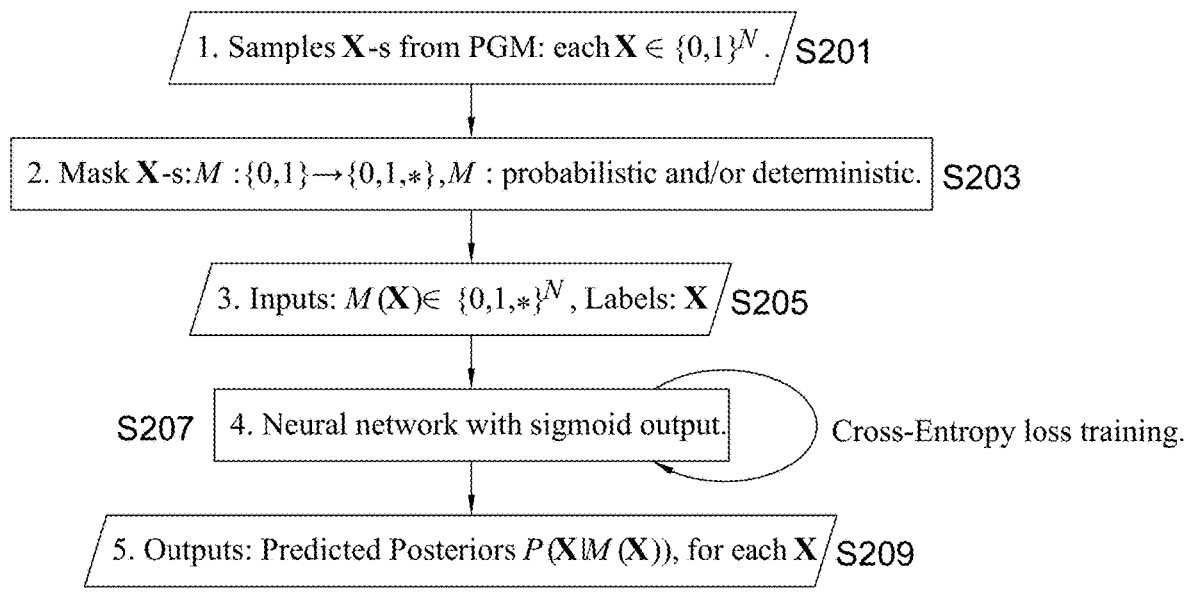
FIG. 3 is a flow diagram showing the training of a discriminative model to use the system of FIG. 1.

The training of the UM will be described in detail with reference to FIG. 3. However, the UM is a model that can approximate the behaviour of the entire PGM 120. In one embodiment the UM is a single neural net, in another embodiment, the model is a neural network which consists of several sub-networks, such that the whole architecture is a form of auto-encoder-like model but with multiple branches. Hence, why "universal" is used in the title of the UM. Further, the UM as will be described with reference to FIG. 3 is trained to be robust to the patient giving incomplete answers. This is achieved via the masking procedure for training the UM that will be described with reference to FIG. 3.

In step S115, the UM returns probabilities to be used as proposals to the inference engine 109. The inference engine 109 then performs importance sampling using the proposals from the UM as estimates and the PGM 120.

The inference engine 109 calculates "likelihood" (conditional marginal probability) P(Disease_i|Evidence) for all diseases.

In addition the inference engine can also determine:
P(Symptom_i|Evidence),
P(Risk factor_i|Evidence)

From this, it can transmit back information in step S117 concerning the "likelihood" of a disease given the evidence supplied by the patient 101 to the interface 105. The interface 105 can then supply this information back to the patient in step S119.

The above high-level explanation of the system presumes that the patient provide all possible evidence they can concerning their symptoms and that the system has access to all possible risk factors of which the patient can give a definitive answer. However, in many situations, the patient will only give a fraction of this information as a first input into the system. For example, if the patient has a stomach ache, the patient is likely to indicate that they have a stomach ache, but probably little further information without prompting.

In a further embodiment, the system determines whether further information is required from the patient 101. As explained above, the inference engine 109 determines:
P(Disease_i|Evidence) for all diseases
P(Symptom_i|Evidence),
P(Risk factor_i|Evidence)

It is possible using a value of information analysis (VoI) to determine from the above likelihoods whether asking a further question would improve the probability of diagnosis. For example, if the initial output of the system seems that there are 9 diseases each having a 10% likelihood based on the evidence, then asking a further question will allow a more precise and useful diagnosis to be made. In an embodiment, the next further questions to be asked are determined on the basis of questions that reduce the entropy of the system most effectively.

In one embodiment, the analysis to determine whether a further question should be asked and what that question should be is based purely on the output of the UM 113 that provide an estimate of the probabilities. However, in a further embodiment, the probabilities derive directly from the PGM via importance sampling using the UM used to make this decision.

Figure 2:
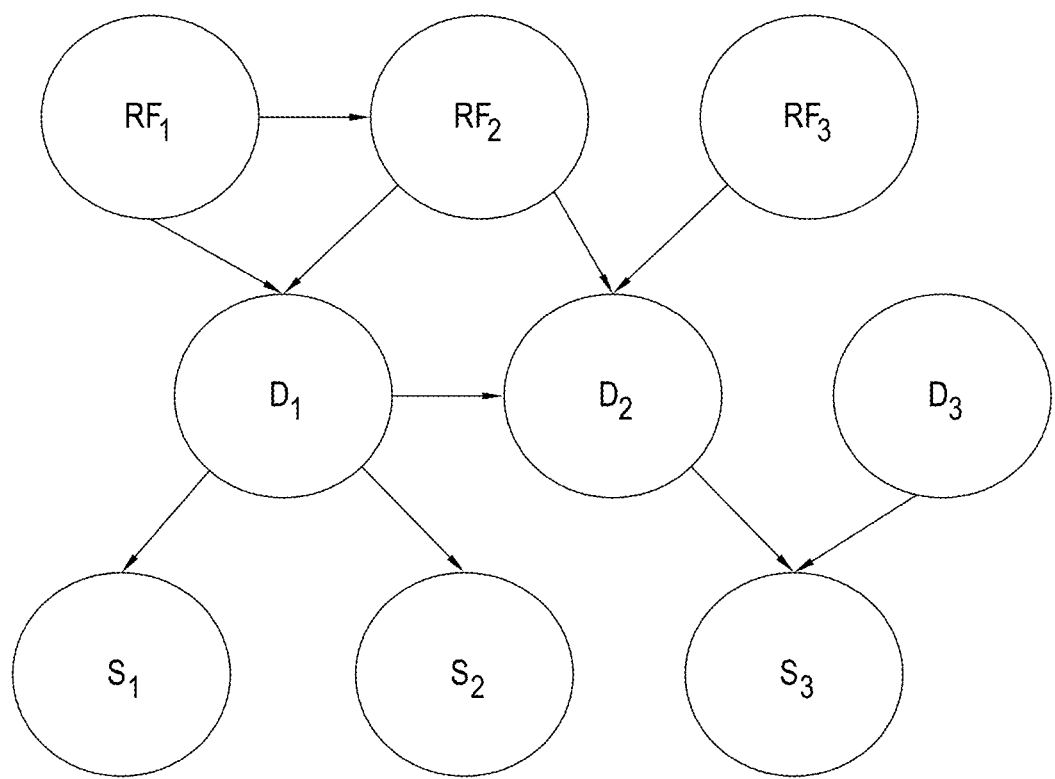
FIG. 2 is a schematic diagram of a simple graphical model.

Once the user supplies further information, then this is then passed back and forth to the inference engine 109 to update evidence to produce updated probabilities. FIG. 2 is a depiction of a graphical model of the type used in the system of FIG. 1.

The graphical model provides a natural framework for expressing probabilistic relationships between random variables, to facilitate causal modelling and decision making. In the model of FIG. 1, when applied to diagnosis, D stands for diagnosis, S for symptom and RF for Risk Factor. Three layers: risk factors, diseases and symptoms. Risk factors causes (with some probability) influence other risk factors and diseases, diseases causes (again, with some probability) other diseases and symptoms. There are prior probabilities and conditional marginals that describe the "strength" (probability) of connections. We use noisy-OR and noisy-MAX modelling assumptions for now.

In this simplified specific example, the model is used in the field of diagnosis. In the first layer, there are three nodes $S_1$, $S_2$ and $S_3$, in the second layer there are three nodes $D_1$, $D_2$ and $D_3$ and in the third layer, there are two nodes $RF_1$, $RF_2$ and $RF_3$.

In the graphical model of FIG. 1, each arrow indicates a dependency. For example, $D_1$ depends on $RF_1$ and $RF_2$. $D_2$ depends on $RF_2$, $RF_3$ and $D_1$. Further relationships are possible. In the graphical model shown, each node is only dependent on a node or nodes from a different layer. However, nodes may be dependent on other nodes within the same layer.

In an embodiment, the graphical model of FIG. 1 is a Bayesian Network. In this Bayesian Network, the network represents a set of random variables and their conditional dependencies via a directed acyclic graph. Thus, in the network of FIG. 2, given full (or partial) evidence over symptoms $S_1$, $S_2$ and $S_3$ and risk factors $RF_1$, $RF_2$ and $RF_3$ the network can be used to represent the probabilities of various diseases $D_1$, $D_2$, and $D_3$.

The BN allows probabilistic inference to update one's beliefs about the likelihood of a set of events, based on observed evidence. However, performing inference on large-scale graphical models is computationally expensive. To reduce the computational task, approximate inference techniques are used variational inference or Monte Carlo methods.

In summary
i. FIG. 2 represents a generative model P(RF,D,S)=P(RF) P(D|RF) P(S|D).
ii. For simplicity for this explanation, it will be assumed that all nodes are binary.
iii. A discriminative model UM is trained (e.g. feedforward neural network) by sampling from the generative model.
iv. Each sample (i.e. combined vector (RF, D, S) becomes a training example.
  1. For the input of one training example, values are "obscured" for each element of the sample vector with some probability. The probability can be different depending on the value of that vector element; if that is the case, the cross-entropy loss should be weighted appropriately by the probability.
  2. The output contains exactly the sample without any obscuring. Each element of the sample vector is a separate independent output node.
v. The loss function is the cross-entropy for each output node.
vi. Since the cross-entropy is used, the discriminative model is expected to learn exactly conditional marginal P (node|partially_obscured(RF, D, S)), where node can be any risk factor, disease or symptom.
vii. This allows the use of the trained discriminative model to either directly approximate the posterior or use that approximation as a proposal for any inference method (e.g. as a proposal for Monte Carlo methods or as a starting point for variational inference, etc).
viii. This conditional marginal approximation can then be used to sample from the joint of the distribution by iterating node by node with less and less risk factors and symptoms obscured.

In the method taught herein, it is possible to provide theoretical guarantees (convergence to the true posterior) regarding the outcomes from inference. This is of particular use when the system is applied to decision making of a sensitive nature e.g. medicine or finance.

In an embodiment, since the true posterior (target distribution) is unknown, the task of inference is to sample from an independent 'proposal' distribution, which ideally, is as close to the target distribution as possible.

When performing inference on Bayesian networks, a prior is often used as the proposal distribution. However, in cases where the BN is used to model rare events, a large number of samples are required to reduce the variance in an estimate of the posterior.

In an embodiment, inference is performed by considering the set of random variables, $X=\{X_1, \ldots X_N\}$. A BN is a combination of a directed acyclic graph (DAG), with $X_i$ as nodes, and a joint distribution of the $X_i$, P. The distribution P can factorize according to the structure of the DAG, $$P(X_1 \ldots, X_n) = \prod_{i=1}^{N} P(X_i | Pa(X_i)) = P(X_1)\prod_{i=2}^{N} P(X_i | X_1, \ldots, X_{i-1}). \quad (1)$$

Where $P(X_i|Pa(X_i))$ is the conditional distribution of Xi given its parents, $Pa(X_i)$. The second equality holds as long as $X_1; X_2; \colon \colon \colon, X_N$ are in topological order.

Now, a set of observed nodes is considered, $\mathbf{X}_O \subset X$ and their observed values $\hat{x}$. To conduct Bayesian inference when provided with a set of unobserved variables, say $X_u \subset X \backslash \mathbf{X}_O$ the posterior marginal is computed:

$$P(X_u | X_O = \hat{x}) = \frac{P(X_u, X_O = \hat{x})}{P(X_O = \hat{x})} = \frac{P(X_u)P(X_O = \hat{x} | X_u)}{P(X_O = \hat{x})} \quad (2)$$

In the optimal scenario, Equation (2) could be computed exactly. However, as noted above exact inference becomes intractable in large BNs as computational costs grow exponentially with effective clique size, —in the worst case, becoming an NP-hard problem In an embodiment, importance sampling is used. Here, a function $f$ is considered for which it's expectation, $E_P[f]$ is to be estimated, under some probability distribution P. It is often the case that we can evaluate P up to a normalizing constant, but sampling from it is costly.

In Importance Sampling, expectation Ep[f] is estimated by introducing a distribution Q, known as the proposal distribution, which can both be sampled and evaluated. This gives:

$$E_p[f] = \int f(x)P(x)dx \quad (3)$$
$$= \int f(x)\frac{P(x)}{Q(x)}Q(x)dx$$
$$= \lim_{n\to\infty} \frac{1}{n}\sum_{i=1}^{n} f(x_i)w_i,$$

Where $x_i \sim Q$ and where $w_i = P(x_i)/Q(x_i)$ are the importance sampling weights. If P can only be evaluated up to a constant, the weights need to be normalized by their sum.

In the case of Inference on a BN, the strategy is to estimate $P(X_u|X_O)$ with an importance sampling estimator if there is appropriate Q to sample from. In the case of using Importance Sampling to sample from the posterior, the weight also contains the likelihood $P(X_O = \hat{x}|X_u)$. Also, while the equalities in (3) hold for any appropriate Q, this is true only in the limit as n→∞ and it is not the case that all importance sampling estimators have the same performance in terms of variance, or equivalently, time till convergence.

For example in likelihood weighting, if $Q=P(X_u)$ is very far from $P(X_u|X_O)$ then, with only a small number of weights dominating the estimate, the variance of the estimator can be potentially huge and the estimation will be poor unless too many samples are generated.

For this reason, the joint distribution $Q=P(X_u|X_O)$ would be the optimal proposal and thus, it would be helpful to obtain an estimate of this to reduce the variance in importance sampling.

In an embodiment a discriminative model UM(:) (a feed-forward neural network or a neural network, with architecture related to auto encoder but with multiple branches) is trained to approximate any possible posterior marginal distribution for any binary BN.

$$Y = UM(X_O) \approx \begin{bmatrix} P(X_1 \mid X_O) \\ P(X_2 \mid X_O) \\ \vdots \\ P(X_n \mid X_O) \end{bmatrix} \quad (4)$$

where n is the total number of nodes, and $X_O$ are the observations. Y is a vector of conditional marginal probabilities for every node in the BN, whether observed or not (if node X_i is observed, the marginal posterior distribution for it will be trial, i.e. $P(X_i|X_O)=1$ or $P(X_i|X_O)=0$).

To approximate any possible posterior marginal distribution i.e., given any possible set of evidence $x_O$, only one model is needed. Due to this the discriminative model is described as a Universal Marginalizer (UM). The existence of such a network is a direct consequence of the universal function approximation theorem (UFAT). This is illustrated by considering marginalization in a BN as a function and that, by UFAT, any measurable function can be arbitrarily approximated by a neural network. Therefore, such a UM can be used as a proposal for the distribution.

The training process for the above described UM involves generating samples from the underlying BN, in each sample masking some of the nodes, and then training with the aim to learn a distribution over this data. This process is explained through the rest of the section and illustrated in FIG. 3.

Such a model can be trained off-line by generating samples from the original BN (PGM 120 of FIG. 1) via ancestral sampling in step S201. In an embodiment unbiased samples are generated from the probabilistic graphical model (PGM) using ancestral sampling. Each sample is a binary vector which will be the values for the classifier to learn to predict.

In an embodiment, for the purpose of prediction then some nodes in the sample then be hidden, or "masked" in step S203. This masking is either deterministic (in the sense of always masking certain nodes) or probabilistic over nodes. In embodiment each node is probabilistically masked (in an unbiased way), for each sample, by choosing a masking probability p~U[0,1] and then masking all data in that sample with probability p. However, in a further embodiment, the masking process is as described in Further Embodiment A.

The nodes which are masked (or unobserved when it comes to inference time) are represented consistently in the input tensor in step S205. Different representations of obscured nodes will be described later, for now, they will be represented them as a '*'.

The neural network is then trained using a cross entropy loss function in step S207 in a multi-label classification setting to predict the state of all observed and unobserved nodes. Any reasonable, i.e., a twice-differentiable norm, loss function could be used. In a further embodiment, the output of the neural net can be mapped to posterior probability estimates. However, when the cross entropy loss is used, the output from the neural net is exactly the predicted probability distribution. In a further embodiment, the loss function is split for different sub-sets of nodes for more efficient learning as described in Further Embodiment A.

The trained neural network can then be used to obtain the desired probability estimates by directly taking the output of the sigmoid layer. This result could be used as a posterior estimate. However, in a further embodiment as described below the UM is combined with importance sampling to improve the accuracy of UM and the speed of importance sampling.

Thus a discriminative model is now produced which, given any set of observations $x_O$, will approximate all the posterior marginals in step S209. Note that the training of a discriminative model can be performed, as often practised, in batches; for each batch, new samples from the model can be sampled, masked and fed to the discriminative model training algorithm; all sampling, masking, and training can be performed on Graphics Processing Units, again as often practised.

This trained Neural net becomes the UM 113 of FIG. 1 and is used to produce the predictions sent to the inference engine 109 in step S115.

In the embodiment, described with reference to FIG. 1, Importance Sampling in the inference engine is augmented by using the predicted posteriors from the UM as the proposals. Using the UM+IS hybrid it is possible to improve the accuracy of results for a given number of samples and ultimately speed up inference, while still maintaining the unbiased guarantees of Importance Sampling, in the limit.

In the above discussion of Importance sampling, we saw that the optimal proposal distribution Q for the whole network is the posterior itself $P(X_u|X_O)$ and thus for each node the optimal proposal distribution is $Q_{opt}=P(X_i \in X_u|$ $X_\mathcal{O} \cup X_S$), where $x_\mathcal{O}$ are the evidence nodes and Xs the already sampled nodes before sampling $X_i$.

As it is now possible, using the above UM to approximate, for all nodes, and for all evidences, the conditional marginal, the sampled nodes can be incorporated into the evidence to get an approximation for the posterior and use it as proposal. For node i specifically, this optimal Q* is:

$$Q^*_i = P(X_i | \{X_1, \ldots, X_{i-1}\} \cup X_\mathcal{O} = \hat{x}) \approx UM(\{X_1, \ldots, X_{i-1}\} \cup X_\mathcal{O})_i = Q_i \quad (5)$$

Figure 4:
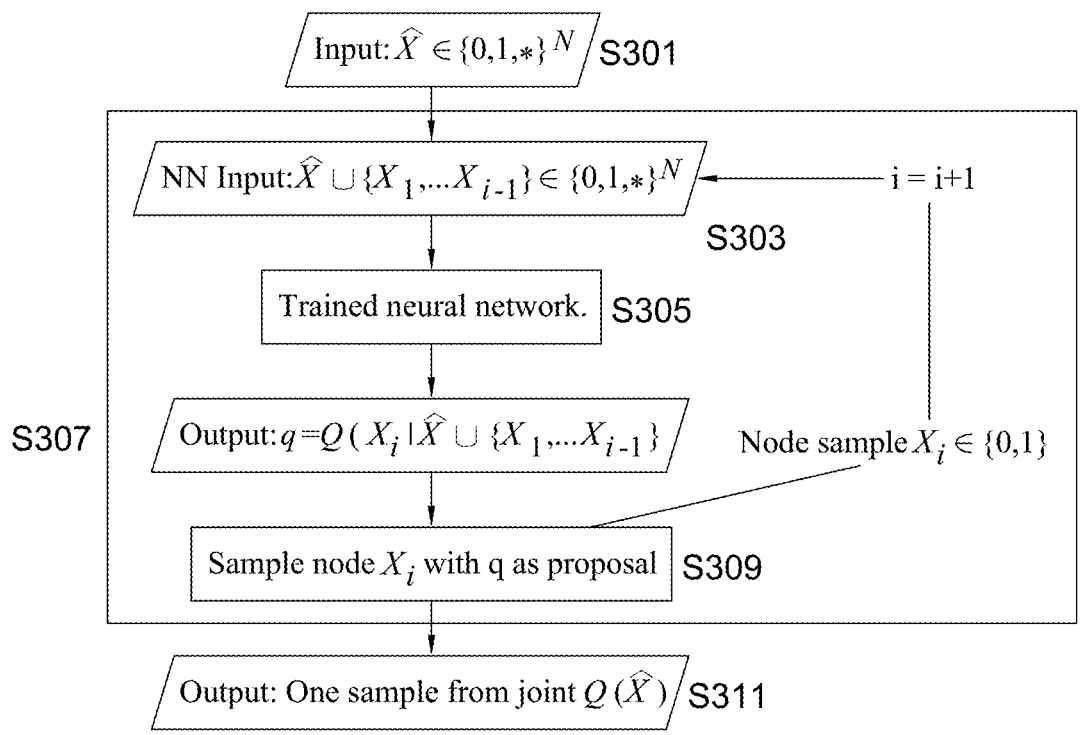
FIG. 4 is a flow diagram showing the use of the trained model with the inference engine of FIG. 1.

The process for sampling from these approximately optimal proposals is illustrated in the algorithm 1 below and in FIG. 4 where the part within the box is repeated for each node in the BN in topological order.

In step S301, the input is received and passed to the UM (NN). The NN input is then provided to the NN (which is the UM) in step S303. The UM calculates in step S305, the output q that it provides in step S307. This is the provided to the Inference engine in step S309 to sample node $X_i$ from the PGM. Then, that node value is injected as an observation into z, and it is repeated for the next node (hence 'i:=i+1'). In step S311, we receive a sample from the approximate joint.

---

Algorithm 1 Sequential Universal Marginalizer importance sampling

1: Order the nodes topologically $X_1, \ldots X_N$, where N is the total number of nodes.
2: for j in [1, ..., M] (where M is the total number of samples): do
3: $\tilde{x}_S = \emptyset$
4: for i in [1, ... N]: do
5: sample node $x_i$ from $Q(X_i) = UM(\tilde{x}_{S \cup O})_i \approx P(X_i | X_S, X_O)$
6: add $x_i$ to $\tilde{x}_S$
7: $[x_S]_j = \tilde{x}_S$ 8:
$$w_j = \prod_{i=1}^{N} \frac{P_i}{Q_i} \text{(where } P_i \text{ is the likelihood, } P_i = P(X_i = x_i | x_{S \cap Pa(X_i)})$$
and $Q_i = Q(X_i = x_i))$ 9:
$$E_p[X] = \frac{\sum_{j=1}^{M} X_j w_j}{\sum_{j=1}^{M} w_j} \text{ (as in standard IS)}$$

---

That is, following the requirement that parents are sampled before their children and adding any previously sampled nodes into the evidence for the next one, we are ultimately sampling from the approximation of the joint distribution. This can be seen by observing the product of the probabilities we are sampling from.

It can be seen that the proposal Q, constructed in such a way, becomes the posterior itself:

$$Q = \prod_{i=1}^{N} Q_i \quad (6)$$

$$= UM(X_O)_i \prod_{i=2}^{N} UM(X_1, \ldots, X_{i-1}, X_O)_i \quad (7)$$

$$\approx P(X_1 | X_O) \prod_{i=2}^{N} P(X_i | X_1, \ldots, X_{i-1}, X_O) \quad (8)$$

$$= P(X_i | X_1, X_2, \ldots, X_n | X_O) \quad (9)$$

This procedure requires that nodes are sampled sequentially, using the UM to provide a conditional probability estimate at each step. This can affect computation time, depending on the parallelization scheme used for sampling. However, parallelization efficiency can be recovered by increasing the number of samples, or batch size, for all steps.

In Importance Sampling, each node will be conditioned on nodes topologically before it. The training process may therefore be optimized by using a "sequential masking" process in the training process as in FIG. 3, where firstly we randomly select up to which node $X_i$ we will not mask anything, and then, as previously, mask some nodes starting from node $X_{i+1}$ (where nodes to be masked are selected randomly, as explained before). This is to perform to a more optimal way of getting training data.

Another way of doing an embodiment might involve a hybrid approach as shown in Algorithm 2 below. There, an embodiment might include calculating the conditional marginal probabilities only once, given the evidence, and then constructing a proposal for each node $X_i$ as a mixture of those conditional marginals (with weight β) and the conditional prior distribution of a node (with weight (1−β)).

---

Algorithm 2 Hybrid UM-IS

1: Order the nodes topologically $X_1, \ldots X_N$, where N is the total number of nodes.
2: for j in [1, ..., M] (where M is the total number of samples): do
3: $\tilde{x}_S = \emptyset$
4: for i in [1, ... N]: do
5: sample node $x_i$ from $Q(X_i) = \beta UM_i(\tilde{x}_O) + (1 - \beta)P$
$(X_i = x_i | x_{S \cap Pa(X_i)})$
6: add $x_i$ to $\tilde{x}_S$
7: $[x_S]_j = \tilde{x}_S$ 8:
$$w_j = \prod_{i=1}^{N} \frac{P_i}{Q_i} \text{(where } P_i \text{ is the likelihood, } P_i = P(X_i = x_i | x_{S \cap Pa(X_i)})$$
and $Q_i = Q(X_i = x_i))$ 9:
$$E_p[X] = \frac{\sum_{j=1}^{M} X_j w_j}{\sum_{j=1}^{M} w_j} \text{ (as in standard IS)}$$

---

While this hybrid approach might be easier and potentially less computationally expensive, in cases when $P(X_i | X_S \cup X_\mathcal{O})$ is far from $P(X_i | X_\mathcal{O})$, this will be just a first-order approximation, hence the variance will be higher and we generally need more samples to get a reliable estimate.

The intuition for approximating $P(X_i | X_\mathcal{O} \cup X_S)$ by linearly combining $P(X_i | Pa(X_i))$ and $UM(X_\mathcal{O})_i$ is simply that $UM(X_\mathcal{O})_i$ will take into account the effect of the evidence on node i and $P(X_i | Pa(X_i))$ will take into account the effect of $X_S$, namely the parents. Note that β could also be allowed to be a function of the currently sampled state and the evidence, for example if all the evidence is contained in parents then=0 is optimal.

Figure 5:
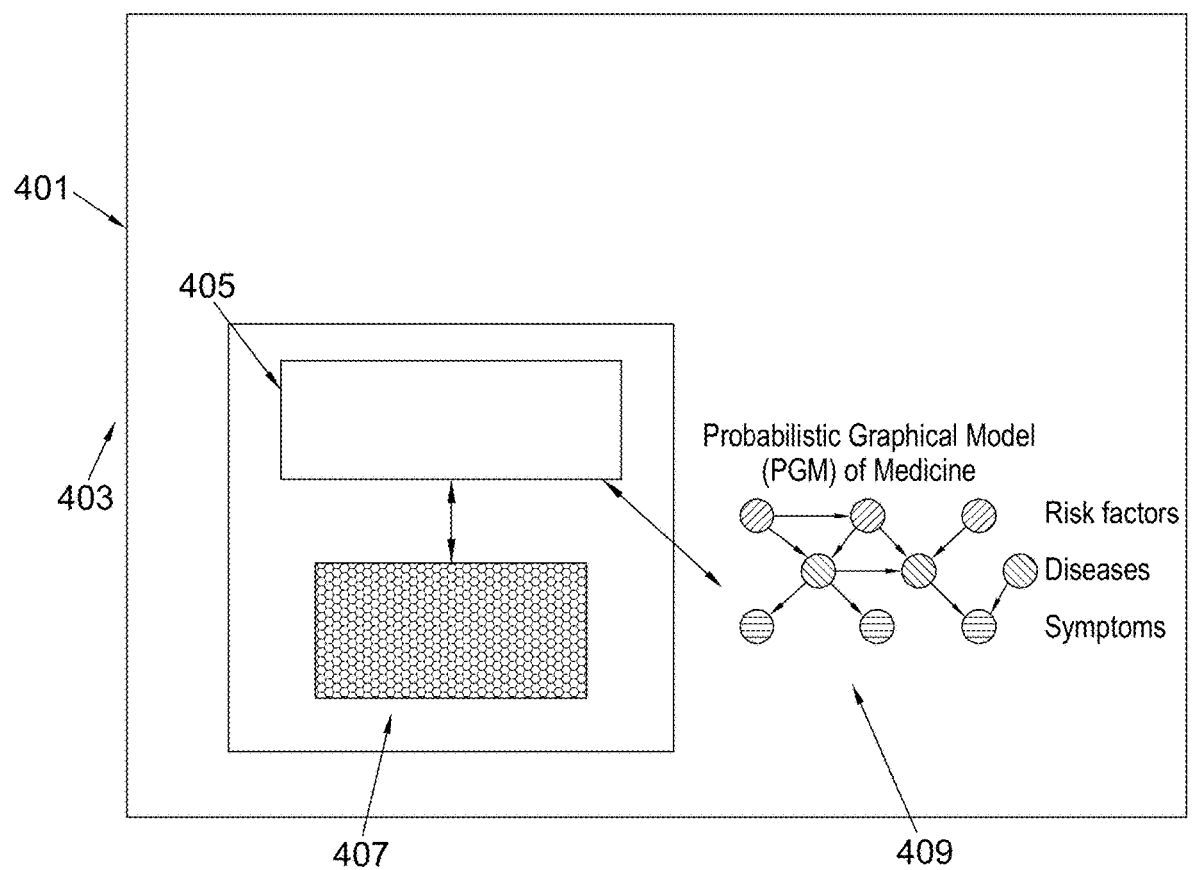
FIG. 5 is a basic schematic processing system with a GPU.

FIG. 5 shows a layout of a system in accordance with a further embodiment of the invention.

The system 401 comprises a processor 403, the processor comprises Computer Processing units (CPUs) 405 and Graphical Processing units (GPUs) 407 that operates under the control of the host. GPUs 407 offer a simplified instruction set that is well suited for a number of numerical applications. Due to the simplified instruction set they are not suitable for any general purpose computing in the same way that CPUs are used, however thanks to these simplifications GPU 407 can offer a much large number of processing cores. This makes GPU 407 ideally suited for applications where computations can be parallelised.

To achieve these performance gains algorithms usually need to be modified to express this parallelism in a form that is easy to implement on GPUs. This can be done either via low level custom GPU instructions (e.g., implementing algorithm in terms of low level CUDA code) or, alternatively, algorithms can be expressed more generally in terms of common vectorised operations, such as scatter, gather, reduce on tensors, as well as higher level numerical routines such as matrix transpose, multiplication, etc.

To express vectorised operations and to make use of higher level tensor frameworks with GPU support, it is possible to use products such as TensorFlow, PyTorch, etc. Once calculations are expressed in vectorised form, in an embodiment, it is possible to make use of the large number of processing cores in modern GPUs by generating a large batch of random numbers, for the importance sampling procedure. The GPU uses data acquired from the PGM 409.

The above approach using a GPU is used to determine the posterior marginal probabilities $P(D_i|\text{evidence}), P(S_i|\text{evidence})$ and $P(RF_i|\text{evidence})$.

In an embodiment, the Noisy-Or model for the conditional prior probabilities in the PGM is used (see for example Koller & Friedman 2009, Probabilistic Graphical Models: Principles and Techniques The MIT Press). In an embodiment, the procedure is modified to improve the numerical stability and to parallelise the computation of the conditional priors.

To improve numerical accuracy, in an embodiment, most calculations are performed in the log domain. From basic properties of the log function multiplication becomes addition. So in the example of the Noisy-Or model instead of calculating probabilities as a multiplications of lambdas, the sum of $\log(\lambda)$ is computed:

$$P(X_i = F \mid Pa(X_i) = [x_k, \ldots x_l]) = \lambda_0 \prod_{j=k}^{l} x_j \lambda_j = \exp\left(\log(\lambda_0) + \sum_{j=k}^{l} \log(x_j \lambda_j)\right),$$

where $x_j \in \{0,1\}$.

To further improve performance the above is then expressed as a tensor operation. Here, a lambda matrix $\Lambda$, is constructed where $\Lambda jk$ is equal to the log lambda value of node j with node k, with $\Lambda jk=0$ if node k is not a parent of node j. $P(X_i|Pa(X))=f([x_k \ldots x_l])$ can be then expressed as a $\Sigma \Lambda_{j,*} S$, where S is the samples tensor and * denotes element-wise multiplication.

To illustrate this, firstly, the likelihood weighting method is shown. The following procedure generates one sample using likelihood weighting. A sample is a full instantiation of the network that is all nodes in the network will be assigned a state. Nodes that are in the evidence set E will be set to their observed state, whereas nodes not in the evidence will be randomly sampled according to their conditional probability given their parents' state.

Procedure Generate-LW-Sample (
    B, // Bayesian network over X
    E = e, // Evidence
)
// conditional probabilities below are calculated using Noisy-Or model
Let X_1, ..., X_n be a topological ordering of X
w =1
for i = 1, ..., n
    u_i = x<Pa(X_i)> // get the sampled state of the parents of X_i
    if X_i not in E then // if X_i not in evidence then sample
        x_i = sample from P(X_i | u_i)
    else
        x_i = e<X_i> // evidence state of X_i in z
        w = w * P(X_i | u_i) // multiply weight by probability of the
    evidence state given the node's parents
return (x_1, ..., x_n), w It is then possible to estimate a probability query y by generating M samples by repeating calling the procedure above M times and then calculate the estimate as:

$$P(y \mid E) = \frac{\sum_{m=1}^{M} w[m] = I\{y[m] = y\}}{\sum_{m=1}^{M} w[m]}$$

Where I is an indicator function which is equal to 1 if the sampled state y of sample m is the same as the target y. In binary nodes, it just means that all weights are summed where y is true and divide that by the total sum of weights.

This procedure can then be extended for importance sampling as follows:

Procedure Generate-IS-Sample (
    B, // Bayesian network over X
    E = e, // Evidence Q // proposal probability distribution
)
// conditional probabilities below are calculated using Noisy-Or model
Let X_1, ..., X_n be a topological ordering of X
w = 1
for i = 1, ..., n
    u_i = x<Pa(X_i)> // get the sampled state of the parents of X_i
    if X_i not in E then // if X_i not in evidence then sample
        p = P(X_i | u_i)
        q = Q(X_i | u_i, E)
        x_i = sample from q
        w = w * (p / q)
    else
        x_i = e<X_i> // evidence state of X_i in z
        w = w * P(X_i | u_i) // multiply weight by probability of the
    evidence state given the node's parents
return (x_1, ..., x_n), w The main difference here is that instead of sampling directly from P it is now possible to sample from Q and correct the weight by the ratio p/q. This can be parallelized on a GPU by simply generating a batch of multiple samples at a time:

Procedure IS-Generate-Batch-of-Samples (
    B, // Bayesian network over X
    E = e, // Evidence

```
Q, // proposal probability distribution
K // batch size
) // conditional probabilities below are calculated using Noisy-Or model
Let X_1, ..., X_n be a topological ordering of X
w = [1, ..., 1] // vector of weights of size Kx1
for i = 1, ..., n
u_i = x<Pa(X_i)> // get the sampled state of the parents of X_i in each sample in the batch,
dimension is Kx1
if X_i not in E then // if X_i not in evidence then sample
p = P(X_i | u_i)
q = Q(X_i | u_i, E)
    x_i = sample K times from q // dimension Kx1
w = w * (p / q) // multiply each element of w by p/q
else
x_i = e<X_i> // evidence state of X_i in z, Kx1 dimension
w = w * P(X_i | u_i) // multiply weight by probability of the evidence state given the
node's parents, Kx1 dimension
return [(x_1, ..., x_n)_1, ..., (x_1, ..., x_n)_K] , w // returns K samples and K weights
```

It is possible to make significant improvements to the efficiency of the tensor representation by optimising the number and size of the tensors used to represent the network—essentially representing the network by a number of 'layers' upon which independent sampling/calculations can be performed. Working with smaller tensors increases the speed of computation for the numerous tensor manipulations used throughout the inference process, but at the expense of increasing the number of those manipulations required due to the increased number of tensors representing the same network.

To optimise the decomposition of the network into layers, the topologically sorted list of network nodes is split into multiple potential 'layers' according via a grid search over three parameters based on the size of tensors created by each layer, namely:

the minimum tensor size
the maximum tensor size
the total 'waste' incurred due to the sequentially increasing tensor size The resultant layers at each grid point are tested according to the metric:
M=(10*number_of_layers)+total_waste Where the total_waste is calculated as the penalty incurred by the incremental increase in individual layer's tensor size. The group of layers with the lowest M are chosen as the optimum representation.

To improve sampling efficiency, in an embodiment, the current estimate of the posterior being calculated was mixed into the Importance Sampling proposal distribution Q. It was found that this helps with convergence. To calculate the current estimate the same probability query formula as above was used with the samples generated so far.

$$q'(X\_i|u\_i,E)=(1-\alpha)*q(X\_i|u\_i,\text{Evidence})+\alpha*\text{current\_estimate of } P(X\_i|\text{Evidence})$$

In a further embodiment, proposal probabilities q were kept within a max precision range to sampling efficiency of the importance sampler in some cases by requiring less samples to arrive at a target accuracy.

Clipping is performed as follows:
  clipped_q=min(max(q, ε), 1−ε)
Here ε was set to 0.001.

In a further embodiment, for importance sampling q was imposed (i.e. by redefining the proposal q:=clipping(q)) to be not too different from p in order to reduce the variance of the weights. One simple heuristic that was found useful was to ensure that q is such that $$\frac{\gamma p}{p+\gamma-1} < \frac{p}{q} < \gamma$$

holds, with a typical value for γ of 2.

In a yet further embodiment, for some nodes an extension to the noisy-OR model was employed which is particularly useful for medical diagnosis, namely the noisy-MAX model. For a binary disease node, the noisy-OR model allows for a child node representing a symptom to be binary (e.g. absent|present). The noisy-MAX model however allows nodes to have one of a variety of states. Therefore for a symptom node it becomes possible to encode the severity of the symptom, for example, by any number of particular states (e.g. absent|mild|strong|severe). Whereas in the noisy-OR model each node-parent connection is described by a single probability parameter (lambda), the noisy-MAX algorithm requires multiple parameters describing the variety of multiple states in which the node can exist. Noisy-MAX nodes are therefore implemented as well on GPUs in our embodiment by adding an additional dimension to the probability value lambda matrix, and producing categorical samples according to the values in this dimension (i.e. sampling from a number of possible states, as opposed to simply true/false).

A demonstration of the above is presented in Further Embodiment A.

In addition to demonstrate the above, the following experiments were performed:

The UM network was trained using cross-entropy loss. Specifically, ReLU non-linearity was used with an applied dropout of 0.5 before each hidden layer and the Adam optimizer was used.

As noted above, there are many options for ways to represent the unobserved nodes on the input layer of the neural network when training the UM as explained with reference to FIG. 3.

Three representations were trialled:

1. 32-bit Continuous Representation Represent false as 0, true as 1 and the unobserved values by a point somewhere between 0 and 1. This is analogous to the probability of the input being true. Three values were used for unobserved: 0, 0.5 and the prior of the node.

2. 2-bit Representation Here, 1 bit was used to represent whether the node is observed and another node to represent whether it is true. {(Observed, True), (Observed, False), (Unobserved, False)}={(1,1),(1,0),(0,0)} which is equivalent to {True, False, Unobserved}={1,2,3} in terms of information.

3. 33-bit Representation (1 bit+Continuous) The further option is to combine these two approaches to allow one bit to represent whether the node is observed or not and another variable to be a float between 0 and 1 to represent the probability of this being true.

To measure the quality of the conditional marginals in themselves, a test set of some evidences. For each evidence, "ground truth" posterior marginals were calculated via Likelihood Sampling with 300 million samples. Then two main metrics were used to assess the quality of the distributions. Firstly the mean absolute error—which calculates the absolute error between the true node posterior and predicted node posterior, then averaged over the test set of evidences.

The second metric is the max error—this looks for the maximum probability error across all nodes in the predictions and then averages these over data points. A grid search was run on network size and unobserved representation and the results are reported using the two metrics in table 1.

TABLE 1 avg error/max error for 20,000 iterations

| | 2 bit | 33 bit (priors) |
|---|---|---|
| [2048] | 0.0063/0.3425 | 0.0060/0.3223 |
| [4096] | 0.0053/0.2982 | 0.0052/0.2951 |
| [1024, 1024] | 0.0081/0.4492 | 0.0083/0.4726 |
| [2048, 2048] | 0.0071/0.4076 | 0.0071/0.4264 |

It can be seen that the largest one layer network performs the best. The difference between the two representations is not large, but the results suggest that providing the priors may help improve performance.

Next, experiments were performed to assess the use of UM posterior estimates as proposals.

To do this comparison, the error to the test set over time was evaluated as the number of samples increases. This was done for a standard likelihood weighting and also Importance Sampling with the UM marginals as a proposal distribution. Again both average absolute and max errors over all the case cards were measured.

Firstly the approximate joint distribution as described above was used with empirically a very good beta of 0.1. With beta of 0.1 equivalent results in 250 k samples were seen as in likelihood weighting 750 k samples, so already this is a 3× speed up.

Although the above has been described in relation to medical data, the above system could also be used for any determination process where there are a plurality of inter-linked factors which are evidenced by observations and a determination of a probable cause is required. For example, the above method can be used in financial systems.

Also, although the above has used the output of the discriminative model as an aid in conducting approximate inference, in some cases, the estimate produced by the discriminative model may be used on its own. Also, the embeddings of such discriminative models (e.g. neural networks) can serve as a vectorised representation of the provided evidence for tasks like classification and clustering or interpretation of node relationships, as described in further embodiment A.

Further Embodiment A

Figure 6:
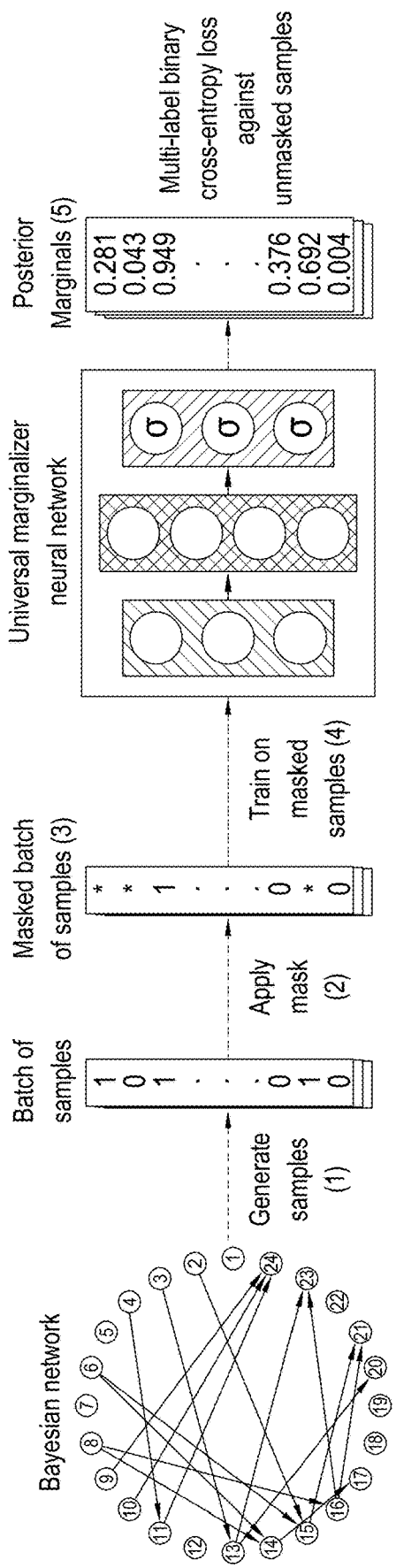
FIG. 6 is a schematic of an overview of a system in accordance with an embodiment.

An framework for the embodiments described herein is shown in FIG. 6 that shows the Universal Marginaliser (UM): The UM performs scalable and efficient inference on graphical models. This figure shows one pass through the network. First, (1) a sample is drawn from the PGM, (2) values are then masked and (3) the masked set is passed through the UM, which then, (4) computes the marginal posteriors.

As described above, probabilistic graphical models are powerful tools that allow formalisation of knowledge about the world and reason about its inherent uncertainty. There exist a considerable number of methods for performing inference in probabilistic graphical models; however, they can be computationally costly due to significant time burden and/or storage requirements; or they lack theoretical guarantees of convergence and accuracy when applied to large scale graphical models. To this end, the above described Universal Marginaliser Importance Sampler (UM-IS) is implemented—a hybrid inference scheme that combines the flexibility of a deep neural network trained on samples from the model and inherits the asymptotic guarantees of importance sampling. The embodiment described herein shows how combining samples drawn from the graphical model with an appropriate masking function allows training of a single neural network to approximate any of the corresponding conditional marginal distributions, and thus amortise the cost of inference. It is also shown that the graph embeddings can be applied for tasks such as: clustering, classification and interpretation of relationships between the nodes. Finally, the method is benchmarked on a large graph (>1000 nodes), showing that UM-IS outperforms sampling-based methods by a large margin while being computationally efficient.

In this embodiment, the Universal Marginaliser Importance Sampler (UM-IS), an amortised inference-based method for graph representation and efficient computation of asymptotically exact marginals is used. In order to compute the marginals, the UM still relies on Importance Sampling (IS). A guiding frame-work based on amortised inference is used that significantly improves the performance of the sampling algorithm rather than computing marginals from scratch every time the inference algorithm is run. This speed-up allows the application of the inference scheme on large PGMs for interactive applications with minimum errors. Furthermore, the neural network can be used to calculate a vectorised representation of the evidence nodes. This representation can then be used for various machine learning tasks such as node clustering and classification.

The main contributions of this embodiment are as follows:

UM-IS is used as a novel algorithm for amortised inference-based importance sampling. The model has the flexibility of a deep neural network to perform amortised inference. The neural net-work is trained purely on samples from the model prior and it benefits from the asymptotic guarantees of importance sampling.

The efficiency of importance sampling is significantly improved, which makes the proposed method applicable for interactive applications that rely on large PGMs.

It will be shown on a variety of toy network and on a medical knowledge graph (>1000 nodes) that the proposed UM-IS outperforms sampling-based and deep learning-based methods by a large margin, while being computational efficient.

It will be shown that the networks embeddings can serve as a vectorised representation of the provided evidence for tasks like classification and clustering or interpretation of node relationships.

As described above, the Universal Marginaliser (UM) is a feed-forward neural network, used to perform fast, single-pass approximate inference on general PGMs at any scale. The UM can be used together with importance sampling as the proposal distribution, to obtain asymptotically exact results when estimating marginals of interest. This hybrid model will be referred to as the Universal Marginaliser Importance Sampler (UM-IS).

As described above, a Bayesian Network (BN) encodes a distribution P over the random variables $X=\{X_1, \ldots, X_N\}$ through a Directed Acyclic Graph (DAG), the random variables are the graph nodes and the edges dictate the conditional independence relationships between random variables. Specifically, the conditional independence of a random variable $X_i$ given its parents $pa(X_i)$ is denoted as $P(X_i|pa(X_i))$.

The random variables can be divided into two disjoint sets, $X_O \subset X$ the set of observed variables within the BN, and $X_u \subset X \backslash X_O$ the set of the unobserved variables.

In this embodiment, a Neural Network (NN) is implemented as an approximation to the marginal posterior distributions $P(X_i|X_O=x_O)$ for each variable $X_i \in X$ given an instantiation $x_O$ of any set of observations. $\tilde{x}_O$ is defined as the encoding of the instantiation that specifies which variables are observed, and what their values are. For a set of binary variables $X_i$ with $i \in 0, \ldots, N$, the desired network maps the N-dimensional binary vector $\tilde{x}_O \subset B^N$ to a vector in $[0,1]^N$ representing the probabilities $p_i := P(1|X_O=x_O)$:

$$Y = UM(\tilde{x}_O) \approx (p_1, \ldots, p_N). \quad (A.1)$$

This NN is used as a function approximator, hence, it can approximate any posterior marginal distribution given an arbitrary set of evidence $X_O$. For this reason, this discriminative model is termed the Universal Marginaliser (UM). If the marginalisation operation in a Bayesian Network is considered as a function $f:B^N \rightarrow [0, 1]^N$, then existence of a neural network which can approximate this function is a direct consequence of the Universal Function Approximation Theorem (UFAT). It states that, under mild assumptions of smoothness, any continuous function can be approximated to an arbitrary precision by a neural network of a finite, but sufficiently large, number of hidden units. Once the weights of the NN are optimised, the activations of those hidden units can be computed to any new set of evidence. They are a compressed vectorised representation of the evidence set and can be used for tasks such as node clustering or classification.

Next, each step of the UM's training algorithm for a given PGM will be described. This model is typically a multi-output NN with one output per node in the PGM (i.e. each variable $X_i$). Once trained, this model can handle any type of input evidence instantiation and produce approximate posterior marginals $P(X_i=1|X_O=\tilde{x}_O)$.

Figure 7:
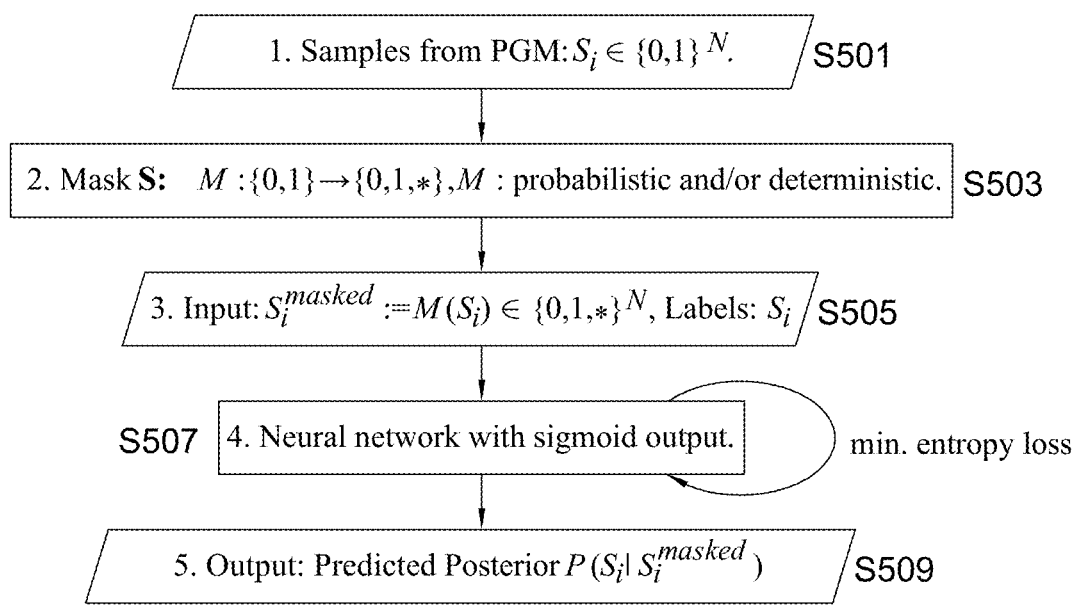
FIG. 7 is a flow diagram showing the training of a discriminative model to use the system of FIG. 6.

The flow chart with each step of the training algorithm is depicted in FIG. 7. For simplicity, it will be assumed that the training data (samples for the PGM) is pre-computed, and only one epoch is used to train the UM.

In practice, the following steps 1-4 are applied for each of the mini-batches separately rather than on a full training set all at once. This improves memory efficiency during training and ensures that the network receives a large variety of evidence combinations, ac-counting for low probability regions in P. The steps are given as follows:

1. S501 Acquiring samples from the PGM. The UM is trained offline by generating unbiased samples (i.e., complete assignment) from the PGM using ancestral sampling. The PGM described here only contains binary variables $X_i$, and each sample $S_i \in B^N$ is a binary vector. In the next steps, these vectors will be partially masked as input and the UM will be trained to reconstruct the complete unmasked vectors as output.

2. S503 Masking. In order for the network to approximate the marginal posteriors at test time, and be able to do so for any input evidence, each sample $S_i$ is partially masked. The network will then receive as input a binary vector where a subset of the nodes initially observed were hidden, or masked. This masking can be deterministic, i.e., always masking specific nodes, or probabilistic. Here a different masking distribution is used for every iteration during the optimization process. This is achieved in two steps. First, two random numbers from a uniform distribution $i,j \sim U[0,N]$ are sampled where N is the number of nodes in the graph. Next, making is performed from randomly selected i (j) number of nodes the positive (negative) state. In this way, the ratio between the positive and negative evidence and the total number of masked nodes is different with every iteration. A network with a large enough capacity will eventually learn to capture all these possible representations.

There is some analogy here to dropout in the input layer and so this approach could work well as a regulariser, independently of this problem. However, it is not suitable for this problem because of the constant dropout probability for all nodes.

3. S505 Encoding the masked elements. Masked elements in the input vectors $S^{masked}$ artificially reproduce queries with unobserved variables, and so their encoding must be consistent with the one used at test time. The encodings are detailed below.

4. S507 Training with Cross Entropy Loss. The NN was trained by minimising the multi-label binary cross entropy of the sigmoid output layer and the unmasked samples $S_i$.

5. S509 Outputs: Posterior marginals. The desired posterior marginals are approximated by the output of the last NN-layer. These values can be used as a first estimate of the marginal posteriors (UM approach); however, combined with importance sampling, these approximated values can be further refined (UM-IS approach).

The UM is a discriminative model which, given a set of observations $X_O$, will approximate all the posterior marginals. While useful on its own, the estimated marginals are not guaranteed to be unbiased. To obtain a guarantee of asymptotic unbiasedness while making use of the speed of the approximate solution, the estimated marginals are used for proposals in importance sampling. A naïve approach is to sample each $X_i \in X_u$ independently from $UM(\tilde{x}_O)_i$, where $UM(\tilde{x}_O)_i$ is the i-th element of vector $UM(\tilde{x}_O)$. However, the product of the (approximate) posterior marginals may be very different to the true posterior joint, even if the marginal approximations are good.

The universality of the UM makes the following scheme possible, which will be termed the Sequential Universal Marginaliser Importance Sampling (SUM-IS). A single proposal is sampled $x_s$ sequentially as follows. First, a new partially observed state is introduced $\tilde{x}_{SUO}$ and it is initialised to $\tilde{x}_O$. Then, $[x_s]_1 \sim UM(\tilde{x}_O)_1$ is sampled and the previous sample $\tilde{x}_{SUO}$ is updated such that $X_1$ is now observed with this value. This process is repeated, at each step sampling $[x_s]_1 \sim UM(\tilde{x}_{SUO})_1$, and $\tilde{x}_{SUO}$ is updated to include the new sampled value. Thus, the conditional marginal can be approximated for a node i given the current sampled state $x_S$ and evidence $X_O$ to get the optimal proposal $Q^*_i$ as follows:

$$Q^*_i = (X_i | \{X_1, \ldots X_{i-1}\} \cup X_O) \approx UM(\tilde{x}_{S \cup O})_i; \quad (A.2)$$

Thus, the full sample $x_S$ is drawn from an implicit encoding of the approximate posterior joint distribution given by the UM. This is because the product of sampled probabilities from Equation A.3 is expected to yield low variance importance weights when used as a proposal distribution.

$$Q = UM(\tilde{x}_O)_1 \prod_{i=2}^{N} UM(\tilde{x}_{S \cup O})_i \quad (A.3)$$

$$\approx P(X_1 | X_O) \prod_{i=2}^{N} P(X_i | X_1, \ldots, X_{i-1}, X_O). \quad (A.4)$$

Figure 8:
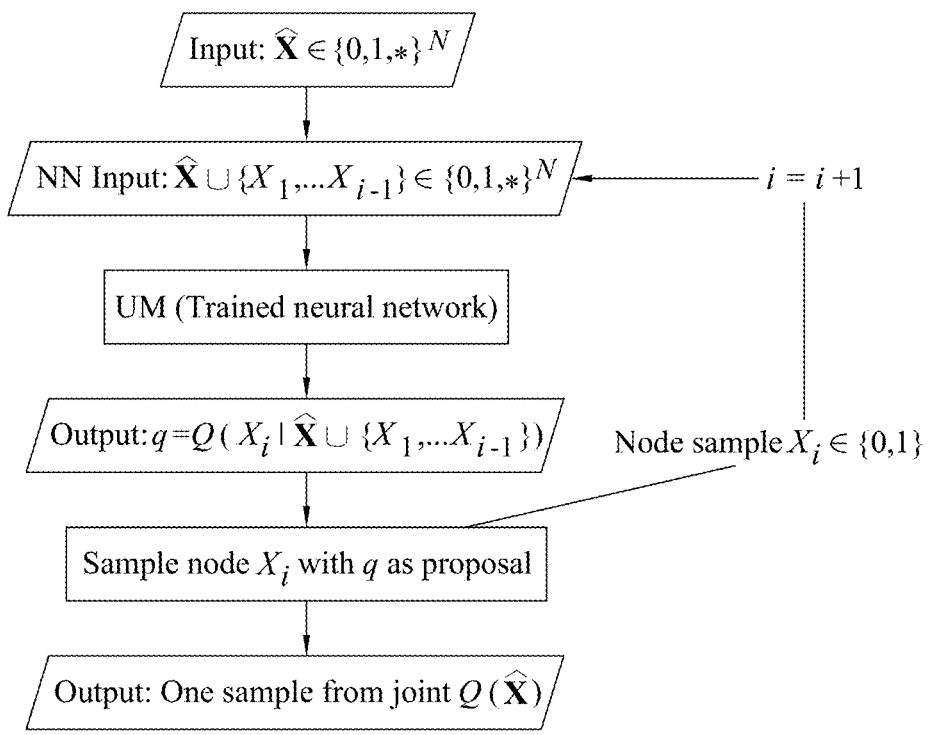
FIG. 8 is a flow diagram showing the use of the trained model with the inference engine of FIG. 6.

The process for sampling from these proposals illustrated in Algorithm 1A and in FIG. 8. The nodes are sampled sequentially using the UM to provide a conditional probability estimate at each step. This requirement can affect computation time, depending on the parallelisation scheme used for sampling. In our experiments, we observed that some parallelisation efficiency can be recovered by increasing the number of samples per batch. Algorithm 1A Sequential Universal Marginalizer importance sampling 1: Order the nodes topologically $X_1, \ldots X_N$, where N is the total number of nodes.
2: for j in [1, ..., M] (where M is the total number of samples): do
3:     $\tilde{x}_S = \emptyset$
4:     for i in [1, ... N]: do
5:        sample node $x_i$ from $Q(X_i) = UM(\tilde{x}_{S \cup O})_i \approx P(X_i | X_S, X_O)$
6:        add $x_i$ to $\tilde{x}_S$
7:     $[x_S]_j = \tilde{x}_S$
8:
$$w_j = \prod_{i=1}^{N} \frac{P_i}{Q_i} \text{(where } P_i \text{ is the likelihood, } P_i = P(X_i = x_i | x_{S \cap pa(X_i)}))$$
and $Q_i = Q(X_i = x_i))$
9:
$$E_p[X] = \frac{\sum_{j=1}^{M} X_j w_j}{\sum_{j=1}^{M} w_j} \text{ (as in standard IS)}$$

Figure 9A:
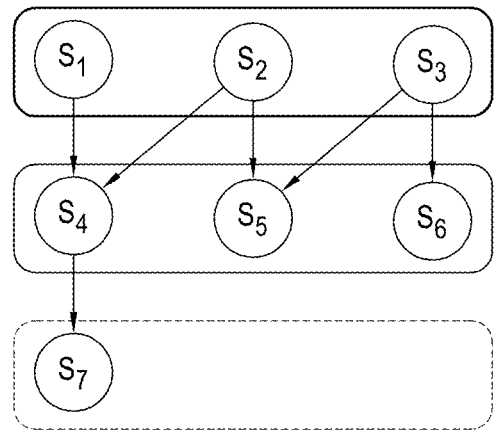
FIG. 9($a$) is a schematic of a graphical Model and FIG. 9($b$) the corresponding UM architecture. The nodes of (a) the graph are categorized by their depth inside the network and the weights of (b) the UM neural network are shared for nodes of the same category.
Figure 9B:
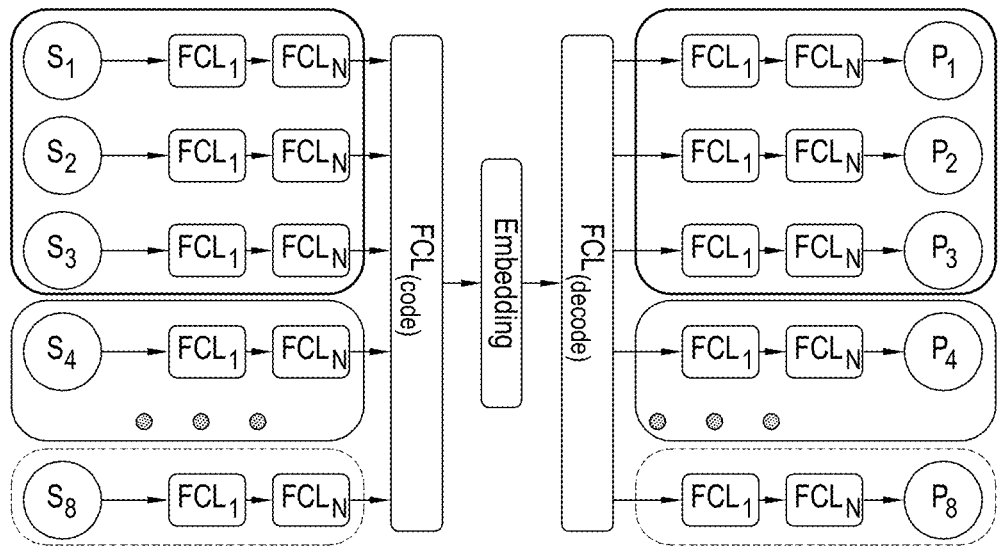

The architecture of the UM is shown in FIG. 9. It has a denoising auto-encoder structure with multiple branches—one branch for each node of the graph. In the experiments, it was noticed that the cross entropy loss for different nodes highly depends on the number of parents and its depth in the graph. To simplify the network and reduce the number of parameters, the weights of all fully connected layers that correspond to specific type of nodes are shared. The types are defined by the depth in the graph (type 1 nodes have no parents, type 2 nodes have only type 1 nodes as parents etc.). The architecture of the best performing model on the large medical graph has three types of nodes and the embedding layer has 2048 hidden states.

In experiments, the best performing UM was chosen in terms of Mean Absolute Error (MAE) on the test set for the subsequent experiments. ReLU non-linearities, apply dropout was used on the last hidden layer and the Adam optimization method was used with batchsize of 2000 samples per batch for parameter learning. Batch normalization was also used between the fully connected layers. To train the model on a large medical graphical model, in total a stream of $3 \times 10^{11}$ samples was used, which took approximately 6 days on a single GPU.

Experiments were performed on a large (>1000 nodes) proprietary Bayesian Network for medical diagnosis representing the relationships between risk factors, diseases and symptoms. An illustration of the model structure is given in FIG. 10(c). Different NN architectures were tried with a grid search over the values of the hyperparameters and on the number of hidden layers, number of states per hidden layer, learning rate and strength of regularisation through dropout.

The quality of approximate conditional marginals was measured using a test set of posterior marginals computed for 200 sets of evidence via ancestral sampling with 300 million samples. The test evidence set for the medical graph was generated by experts from real data. The test evidence set for the synthetic graphs was sampled from a uniform distribution. Standard importance sampling was used, which corresponds to the likelihood weighting algorithm for discrete Bayesian networks with 8 GPUs over the course of 5 days to compute precise marginal posteriors of all test sets.

Two main metrics are considered: the Mean Absolute Error (MAE) given by the absolute difference of the true and predicted node posteriors and the Pearson Correlation Coefficient (PCC) of the true and predicted marginal vectors. Note that we did not observe negative correlations and therefore both measures are bounded between 0 and 1. The Effective Sample Size (ESS) statistic was used for the comparison with the standard importance sampling. This statistics measures the efficiency of the different proposal distributions used during sampling. In this case, there was not access to the normalising constant of the posterior distribution, the ESS is defined as $(\sum_{i=1}^{M} w_i)^2 / \sum_{i=1}^{M} (w_i)^2$, where the weights, $w_i$, are defined in Step 8 of Algorithm 1A.

A one hot encoding was considered for the unobserved and observed nodes. This representation only requires two binary values per node. One value represents if the node is observed and positive ([0,1]) and the other value represents whether this node is observed and negative ([1,0]). If the node is unobserved or masked, then both values are set to zero ([0,0]).

In this section, first the results of different architectures for the UM will be discussed, then the performance of importance sampling will be compared with different proposal functions. Finally, the efficiency of the algorithm will be discussed. A hyperparameter grid search was used on the different network architectures and data representations. The algorithmic performance was not greatly affected for different types of data representations. It is hypothesised that this is due to the fact that neural networks are flexible models capable of handling different types of in-puts efficiently by capturing the representations within the hidden layers. In contrast, the network architecture of the UM strongly depends on the structure of the PGM. For this reason, a specific UM needs to be trained for each PGM. This task can be computation-ally expensive but once the UM is trained, it can be used to compute the approximate marginals in a single forward pass on any new and even unseen set of evidence.

In order to evaluate the performance of sampling algorithms, the change in PCC and MAE on the test sets was monitored with respect to the total number of samples. It was noticed that across all experiments, a faster increase in the maximum value or the PCC is observed when the UM predictions are used as proposals for importance sampling. This effect becomes more pronounced as the size of the graphical model increases. FIG. 10 indicates standard IS (blue line) reaches PCC close to 1 and an MAE close to 0 on the small network with 96 nodes. In this case of very small graphs, both algorithms converge quickly to the exact solution. However, UM-IS (orange-line) still outperforms IS and converges faster, as seen in FIG. 10(a). For the synthetic graph with 798 nodes, standard IS reaches an MAE of 0.012 with $10^6$ samples, whereas the UM-IS error is 3 times lower (0.004) for the same number of samples. The same conclusions can also be drawn for PCC. Most interestingly, on the large medical PGM (FIG. 10(c)), the UM-IS with $10^5$ samples exhibits better performance than standard IS with $10^5$ samples in terms of MAE and PCC. In other words, the time (and computational costs) of the inference algorithm is significantly reduced by factor of ten or more. It was expected for this improvement to be even stronger on much larger graphical models. The results of a simple UM architecture as a baseline are also included. This simple UM (UM-IS-Basic) has one single hidden layer that is shared for all nodes of the PGM. It can be seen that the MAE and PCC still improved over standard IS. However, UM-IS with multiple fully connected layers per group of nodes significantly outperforms the basic UM by a large margin. There are two reasons for this. First, the model capacity of the UM is higher which allows to learn more complex structures from the data. Secondly, the losses in the UM are spread across all groups of nodes and the gradient update steps are optimised with the right order of magnitude for each group. This prevents the model from overfitting to the states of a specific type of node with a significant higher loss.

Figure 11A:
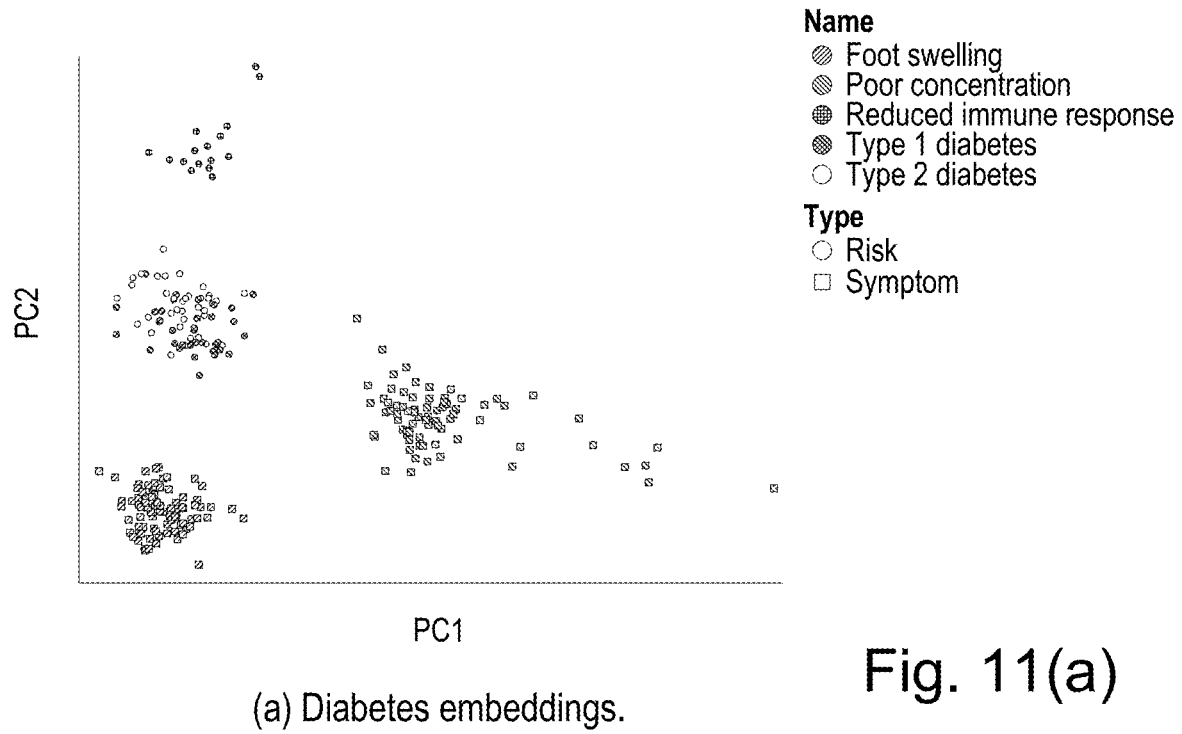
FIG. 11 shows the embeddings filtered for two sets of symptoms and risk factors, where each scatter point corresponds to a set of evidence.
Figure 11B:
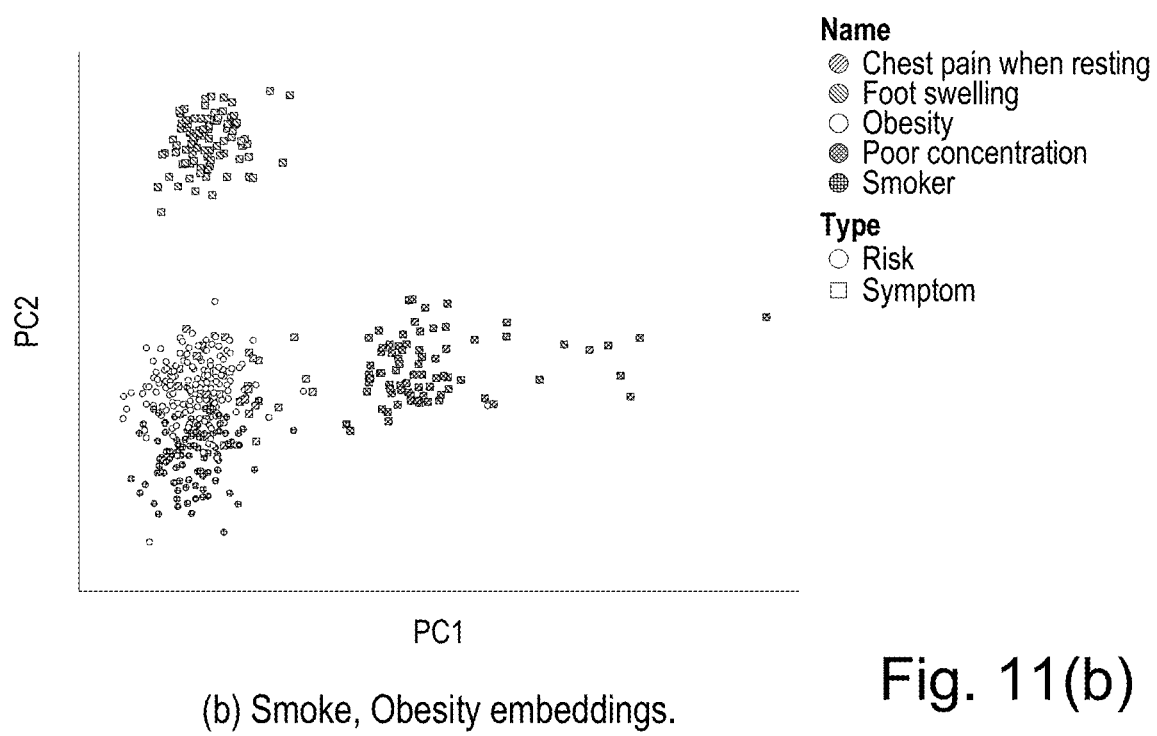

Extracting meaningful representations form the evidence set is an additional interesting feature of the UM. In this section, it is demonstrated that the qualitative results for this application. The graph embeddings are extracted as the 2048 dimensional activations of the inner layer of the UM (see FIG. 9). They are a low-dimensional vectorised representation of the evidence set in which the graphs structure is preserved. That means that the distance for nodes that are tightly connected in the PGM should be smaller than the distance to nodes than are independent. In order to visualise this feature, the first two principal components of the embeddings from different evidence sets are plotted in which it is known that they are related. The evidence set from the medical PGM is used with different diseases, risk-factors and symptoms as nodes. FIG. 11(a) shows that the embeddings of sets with active Type-1 and Type-2 diabetes are collocated. Although the two diseases have different underlying cause and connections in the graphical model (i.e pancreatic beta-cell atrophy and insulin-resistance respectively), they share similar symptoms and complications (e.g cardiovascular diseases, neuropathy, increased risk of infections etc.). A similar clustering can be seen in FIG. 11(b) for two cardiovascular risk factors: smoking and obesity, interestingly collocated with a sign seen in patient suffering from a severe heart condition (i.e unstable angina, or acute coronary syndrome): chest pain at rest.

To further asses the quality of the UM embeddings, experiments are performed for node classification with different features and two different classifiers. More precisely, a SVM and Ridge regression model with thresholded binary output was trained for multi-task disease detection. These models were trained to detect the 14 most frequent diseases from (a) the set of evidence or (b) the embedding of that set. A 5-fold standard cross validation was used with a grid search over the hyperparameter of both models and the number of PCA components for data preprocessing. Table 1A shows the experimental results for the two types of features. As expected, the models that were trained on the UM embeddings reach a significantly higher performance across all evaluation measures. This is mainly because the embeddings of the evidence set are effectively compressed and structured and also preserve the information form the graph structure. Note that the mapping from the evidence set to the embeddings was optimised with a large number of generated samples ($3*10^11$) during the UM learning phase. Therefore, these representations can be used to build more robust machine learning methods for classification and clustering rather than using the raw evidence set to the PGM.

TABLE 1A

Classification performances using two different features.
Each classifier is trained on - dense the dense embedding
as features, and input - the top layer (UM input) as features.
The target (output) is always the disease layer.

| | Linear SVC | | Ridge | |
| --- | --- | --- | --- | --- |
| | dense | input | dense | input |
| F1 | 0.67 ± 0.01 | 0.07 ± 0.00 | 0.66 ± 0.04 | 0.17 ± 0.01 |
| Precision | 0.84 ± 0.03 | 0.20 ± 0.04 | 0.81 ± 0.06 | 0.22 ± 0.04 |
| Recall | 0.58 ± 0.02 | 0.05 ± 0.00 | 0.59 ± 0.04 | 0.16 ± 0.01 |
| Accuracy | 0.69 ± 0.01 | 0.31 ± 0.01 | 0.63 ± 0.02 | 0.27 ± 0.01 |

The above embodiment paper discusses a Universal Marginaliser based on a neural network which can approximate all conditional marginal distributions of a PGM. It is shown that a UM can be used via a chain decomposition of the BN to approximate the joint posterior distribution, and thus the optimal proposal distribution for importance sampling. While this process is computationally intensive, a first-order approximation can be used requiring only a single evaluation of a UM per evidence set. The UM on multiple datasets and also on a large medical PGM is evaluated demonstrating that the UM significantly improves the efficiency of importance sampling. The UM was trained offline using a large amount of generated training samples and for this reason, the model learned an effective representation for amortising the cost of inference. This speed-up makes the UM (in combination with importance sampling) applicable for interactive applications that require a high performance on very large PGMs. Furthermore, the use of the UM embeddings was explored and it has been shown that they can be used for tasks such as classification, clustering and interpretability of node relations. These UM embeddings make it possible to build more robust machine learning applications that rely on large generative models.

Next, for completeness, an overview of importance sampling and how it is used for computing the marginals of a PGM given a set of evidence will be described.

In BN inference, Importance Sampling (IS) is used to provide the posterior marginal estimates $P(X_u|X_O)$. To do so, samples xu are drawn from a distribution $Q(X_u|X_O)$, known as the proposal distribution. The proposal distribution must be defined such that both sampling from and evaluation can be performed efficiently.

Provided that $P(Xu, X_O)$ can be evaluated, and that this distribution is such that Xu contains the Markov boundary of $X_O$ along with all its ancestors, IS states that posterior estimates can be formed as shown in Equation B1 below:

$$P(X_u = x_u | X_O = x_O) = \int 1_{x_u}(x) \frac{P(x | x_O)}{Q(x | x_O)} Q(x | x_O) dx \tag{B1}$$

-continued $$= \frac{Q(x_O)}{P(x_O)} \int 1_{x\mathcal{U}}(x) \frac{P(x, x_O)}{Q(x, x_O)} Q(x \mid x_O) dx$$

$$= \lim_{n \to \infty} \sum_{i=1}^{n} 1_{x\mathcal{U}}(x_i) \frac{w_i}{\sum_{j=1}^{n} w_j},$$

where $x_i \sim Q$ and $w_i = P(x_i, x\sigma)/Q(x_i, x\sigma)$ are the importance sampling weights and $1_{x_u}(x)$ is an indicator function for xu.

The simplest proposal distribution is the prior, P(Xu) However, as the prior and the posterior may be very different (especially in large networks) this is often an inefficient approach. An alternative is to use an estimate of the posterior distribution as a proposal. In this work, we argue that the UM learns an optimal proposal distribution.

In an embodiment, for sampling from the posterior marginal a BN can be considered with Bernoulli nodes and of arbitrary size and shape. Consider two specific nodes, $X_i$ and $X_j$, such that $X_j$ is caused only and always by $X_i$:

$P(X_j=1 \mid X_i=1)=1,$ $P(X_j=1 \mid X_i=0)=0.$

Given evidence E, it can be assumed that $P(X_i|E)=0:001=P(X_j|E)$. It will now be illustrated that using the posterior distribution P (X|E) as a proposal will not necessarily yield the best result.

Say we have been given evidence, E, and the true conditional probability of P $(X_i|E)=0:001$, therefore also P $(X_j|E)=0:001$. It would be naively expected that P(X|E) to be the optimal proposal distribution. However we can illustrate the problems here by sampling with Q=P(X|E) as the proposal.

Each node k∈N will have a weight $w_k=P(X_k)/Q(X_k)$ and the total weight of the sample will be $$w = \prod_{k=0}^{N} w_k.$$

The weights should be approximately 1 if Q is close to P. However, consider the $w_j$. There are four combinations of $X_i$ and $X_j$. $X_i=1$, $X_j=1$ only will be sampled, in expectation, one every million samples, however when the weight is determined $w_j$ will be $w_j=P(X_j=1)/Q(X_j=1)=1=0:001=1000$. This is not a problem in the limit, however if it happens for example in the first 1000 samples then it will outweigh all other samples so far. As soon as there is a network with many nodes whose conditional probabilities are much greater than their marginal proposals this becomes almost inevitable. A further consequence of these high weights is that, since the entire sample is weighted by the same weight, every node probability will be effected by this high variance.

Further embodiments are set out below:

A method, of using the embeddings of using the above discriminative model as a vectorised representation of the provided evidence for classification.

A method of using the embeddings of using the above discriminative model as a vectorised representation of the provided evidence for clustering.

A method of using the embeddings of using the above discriminative model as a vectorised representation of the provided evidence for interpretation of node relationships."

While certain embodiments have been described, these embodiments have been presented by way of example only, and are not intended to limit the scope of the inventions. Indeed the novel methods and systems described herein may be embodied in a variety of other forms; furthermore, various omissions, substitutions and changes in the form of methods and systems described herein may be made without departing from the spirit of the inventions. The accompanying claims and their equivalents are intended to cover such forms of modifications as would fall within the scope and spirit of the inventions.

The invention claimed is:

1. A method for providing a computer implemented medical diagnosis, the method comprising:
   receiving an input from a user comprising at least one symptom;
   providing the at least one symptom as an input to a medical model comprising:
      a probabilistic graphical model, wherein said probabilistic graphical model is a generative model comprising probability distributions and relationships between symptoms and diseases;
      a discriminative model comprising a neural network pre-trained to approximate the probabilistic graphical model, wherein the neural network is configured to approximate any of a plurality of posterior marginal distributions given an arbitrary set of evidence; and
      an inference engine configured to perform Bayesian inference via statistical sampling on said probabilistic graphical model, the inference engine comprising a graphical processing unit and said statistical sampling being performed using parallel processing,
   performing Bayesian inference via statistical sampling on said probabilistic graphical model with said inference engine to obtain a prediction of the probability that the user has a disease comprising:
      performing statistical sampling on said probabilistic graphical model comprising sampling, from one or more posterior marginal distributions, values for each of a plurality of nodes of the probabilistic graphical model, wherein the one or more posterior marginal distributions are derived using the neural network pre-trained to approximate the probabilistic graphical model; and
   outputting the probability of the user having the disease for display by a display device.

2. The method of claim 1, wherein the statistical sampling is implemented via tensor operations.

3. The method of claim 1, wherein the statistical sampling is importance sampling comprising an importance sampling proposal distribution.

4. The method of claim 3, wherein the current estimate of the posterior probability that a user has a disease given the symptoms provided by the user, is mixed with the importance sampling proposal distribution.

5. The method of claim 4, wherein probabilities are clipped.

6. The method of claim 1, wherein during training of the neural network some of the data of the samples has been masked to allow the neural network to produce data which is robust to the user providing incomplete information about their symptoms.

7. The method of claim 1, wherein the inference engine is adapted to perform importance sampling over conditional marginals.

8. The method of claim 1, wherein the neural network comprising a plurality of sub-networks that can approximate the outputs of the probabilistic graphical model.

9. The method of claim 1, wherein the neural network is a single neural network that can approximate the outputs of the probabilistic graphical model.

10. The method of claim 1, wherein the probabilistic graphical model is a noisy-OR model.

11. The method of claim 1, wherein determining the probability that the user has one or more diseases further comprises determining whether further information from the user would improve the diagnosis and requesting further information.

12. The method of claim 1, wherein the medical model receives information concerning the symptoms of the user and risk factors of the user.

13. A non-transitory carrier medium comprising computer readable code configured to cause a computer to perform a method for providing a computer implemented medical diagnosis, the method comprising:
receiving an input from a user comprising at least one symptom;
providing the at least one symptom as an input to a medical model comprising:
a probabilistic graphical model, wherein said probabilistic graphical model is a generative model comprising probability distributions and relationships between symptoms and diseases;
a discriminative model comprising a neural network pre-trained to approximate the probabilistic graphical model, wherein the neural network is configured to approximate any of a plurality of posterior marginal distributions given an arbitrary set of evidence; and
an inference engine configured to perform Bayesian inference via statistical sampling on said probabilistic graphical model, the inference engine comprising a graphical processing unit and said statistical sampling being performed using parallel processing,
performing Bayesian inference via statistical sampling on said probabilistic graphical model with said inference engine to obtain a prediction of the probability that the user has a disease comprising:
performing statistical sampling on said probabilistic graphical model comprising sampling, from one or more posterior marginal distributions, values for each of a plurality of nodes of the probabilistic graphical model, wherein the one or more posterior marginal distributions are derived using the neural network pre-trained to approximate the probabilistic graphical model; and
outputting the probability of the user having the disease for display by a display device.

14. A system for providing a computer implemented medical diagnosis, the system configured to:
receive an input from a user comprising at least one symptom;
provide the at least one symptom as an input to a medical model comprising:
a probabilistic graphical model, wherein said probabilistic graphical model is a generative model comprising probability distributions and relationships between symptoms and diseases;
a discriminative model comprising a neural network pre-trained to approximate the probabilistic graphical model, wherein the neural network is configured to approximate any of a plurality of posterior marginal distributions given an arbitrary set of evidence; and
an inference engine configured to perform Bayesian inference via statistical sampling on said probabilistic graphical model, the inference engine comprising a graphical processing unit and said statistical sampling being performed using parallel processing,
perform approximate inference on the probabilistic graphical model with said inference engine to obtain a prediction of the probability that the user has a disease comprising:
performing statistical sampling on said probabilistic graphical model comprising sampling, from one or more posterior marginal distributions, values for each of a plurality of nodes of the probabilistic graphical model, wherein the one or more posterior marginal distributions are derived using the neural network pre-trained to approximate the probabilistic graphical model; and
output the probability of the user having the disease for display by a display device.

15. The method of claim 1, wherein the probabilistic graphical model comprises at least 96 nodes.

16. The method of claim 1, wherein the probabilistic graphical model comprises at least 768 nodes.

17. The method of claim 1, wherein the probabilistic graphical model comprises a medical knowledge graph comprising at least 1000 nodes.

* * * * *